US010022063B2

(12) United States Patent
Jackson

(10) Patent No.: US 10,022,063 B2
(45) Date of Patent: Jul. 17, 2018

(54) DETERMINING PACED CARDIAC DEPOLARIZATION WAVEFORM MORPHOLOGICAL TEMPLATES

(71) Applicant: Medtronic, Inc., Minneapolis, MN (US)

(72) Inventor: Troy E. Jackson, Corcoran, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/295,352

(22) Filed: Oct. 17, 2016

(65) Prior Publication Data
US 2017/0035315 A1 Feb. 9, 2017

Related U.S. Application Data

(63) Continuation of application No. 14/615,699, filed on Feb. 6, 2015, now Pat. No. 9,468,392.

(51) Int. Cl.
*A61B 5/0464* (2006.01)
*A61B 5/00* (2006.01)
(Continued)

(52) U.S. Cl.
CPC .......... *A61B 5/0464* (2013.01); *A61B 5/1118* (2013.01); *A61B 5/686* (2013.01);
(Continued)

(58) Field of Classification Search
CPC ..... A61B 5/0464; A61B 5/1118; A61B 5/686; A61N 1/3622; A61N 1/371; A61N 1/37205; A61N 1/3937; A61N 1/0587
(Continued)

(56) References Cited

U.S. PATENT DOCUMENTS 5,117,824 A 6/1992 Keimel et al.
5,354,316 A 10/1994 Keimel
(Continued)

FOREIGN PATENT DOCUMENTS

EP 2471452 A1 7/2012
WO 2006116633 A1 11/2006
(Continued)

OTHER PUBLICATIONS

Zhang, "Method and Apparatus for Discriminating Tachycardia Events in a Medical Device Using Two Sensing Vectors," U.S. Appl. No. 14/250,040, filed Apr. 10, 2014, 52 pages.
(Continued)

*Primary Examiner* — Carl H Layno
*Assistant Examiner* — Erin M Piateski

(57) ABSTRACT

Techniques for determining paced cardiac depolarization waveform morphological templates are described. For example, an implantable medical device (IMD) may sense a cardiac electrogram of a heart, identify cardiac depolarizations within the cardiac electrogram, and determine that the cardiac depolarizations are paced cardiac depolarizations resulting from delivery of a pacing pulse to the heart by another IMD without detecting the pacing pulse and without communicating with the other IMD. The IMD may identify paced cardiac depolarization waveforms of the paced cardiac depolarizations, determine a paced cardiac depolarization waveform morphological template based on the identified paced cardiac depolarization waveforms, determine a normal cardiac depolarization waveform morphological template based on the paced cardiac depolarization waveform morphological template, and compare the normal cardiac depolarization waveform morphological template to subsequent cardiac depolarization waveforms. The IMD
(Continued)

may detect a cardiac tachyarrhythmia based on the above comparison.

29 Claims, 15 Drawing Sheets

(51) Int. Cl.
| | |
|---|---|
| *A61B 5/11* | (2006.01) |
| *A61N 1/37* | (2006.01) |
| *A61N 1/39* | (2006.01) |
| *A61N 1/362* | (2006.01) |
| *A61N 1/372* | (2006.01) |
| *A61N 1/05* | (2006.01) |

(52) U.S. Cl.
 CPC ............ *A61N 1/3622* (2013.01); *A61N 1/371* (2013.01); *A61N 1/37205* (2013.01); *A61N 1/3937* (2013.01); *A61N 1/0587* (2013.01)

(58) Field of Classification Search
 USPC ........................................................ 600/510
 See application file for complete search history.

(56) References Cited

U.S. PATENT DOCUMENTS

| | | |
|---|---|---|
| 5,545,186 A | 8/1996 | Olson et al. |
| 5,682,902 A | 11/1997 | Herleikson |
| 5,725,562 A | 3/1998 | Sheldon |
| 6,393,316 B1 | 5/2002 | Gillberg et al. |
| 6,745,068 B2 | 6/2004 | Koyrakh et al. |
| 7,031,771 B2 | 4/2006 | Brown et al. |
| 7,062,315 B2 | 6/2006 | Koyrakh et al. |
| 7,120,491 B1 | 10/2006 | Bailin et al. |
| 7,228,173 B2 | 6/2007 | Cazares |
| 7,242,978 B2 | 7/2007 | Cao et al. |
| 7,283,863 B2 | 10/2007 | Gunderson et al. |
| 7,542,794 B1 | 6/2009 | Zhang et al. |
| 7,930,020 B2 | 4/2011 | Zhang et al. |
| 7,991,467 B2 | 8/2011 | Markowitz et al. |
| 8,160,684 B2 | 4/2012 | Ghanem et al. |
| 8,260,412 B2 | 9/2012 | Krause et al. |
| 8,406,880 B2 | 3/2013 | Yonce et al. |
| 8,437,842 B2 | 5/2013 | Zhang et al. |
| 8,744,572 B1 | 6/2014 | Greenhut et al. |
| 8,750,989 B2 | 6/2014 | Bardy et al. |
| 8,798,745 B2 | 8/2014 | Jacobson |
| 8,805,498 B1 | 8/2014 | Fischell et al. |
| 9,468,392 B2 | 10/2016 | Jackson |
| 2003/0083711 A1 | 5/2003 | Yonce et al. |
| 2005/0131478 A1* | 6/2005 | Kim ..................... A61B 5/7217 607/27 |
| 2005/0137485 A1 | 6/2005 | Cao et al. |
| 2005/0192506 A1* | 9/2005 | Kim ..................... A61B 5/0402 600/510 |
| 2006/0129198 A1 | 6/2006 | Zhang |
| 2007/0249944 A1* | 10/2007 | Fischell ............... A61B 5/0031 600/509 |
| 2009/0099618 A1 | 4/2009 | Rousso et al. |
| 2012/0316613 A1 | 12/2012 | Keefe et al. |
| 2013/0030314 A1 | 1/2013 | Keel et al. |
| 2013/0165988 A1 | 6/2013 | Ghosh |
| 2013/0197599 A1* | 8/2013 | Sambelashvili ....... A61N 1/368 607/25 |
| 2013/0231710 A1* | 9/2013 | Jacobson ............. A61N 1/3708 607/4 |
| 2014/0052012 A1 | 2/2014 | Snell et al. |
| 2014/0276155 A1 | 9/2014 | Zhang |

FOREIGN PATENT DOCUMENTS

| | | |
|---|---|---|
| WO | 2011139686 A1 | 11/2011 |
| WO | 2014120769 A1 | 8/2014 |

OTHER PUBLICATIONS

Greenhut et al., "Method and Apparatus for Adjusting a Blanking Period During Transitioning Between Operating States in a Medical Device," U.S. Appl. No. 14/487,248, filed Sep. 16, 2014, 36 pages.
Zhang, "Method and Apparatus for Verifying Discriminating of Tachycardia Events in a Medical Device Having Dual Sensing Vectors," U.S. Appl. No. 14/255,158, filed Apr. 17, 2014, 65 pages.
(PCT/US2016/016099) PCT Notification of Transmittal of the International Search Report and the Written Opinion of the International Searching Authority, dated May 3, 2016, 12 pages.
Prosecution History from U.S. Appl. No. 14/615,699, dated Feb. 2, 2016 through Jun. 14, 2016, 51 pp.

* cited by examiner

DETERMINING PACED CARDIAC DEPOLARIZATION WAVEFORM MORPHOLOGICAL TEMPLATES

This application is a continuation of U.S. patent application Ser. No. 14/615,699, filed Feb. 6, 2015, now U.S. Pat. No. 9,468,392, issued Oct. 18, 2016, the entire content of which is incorporated herein by reference.

TECHNICAL FIELD

The disclosure relates to medical devices, and, more particularly, to implantable medical devices configured to detect and treat cardiac arrhythmias.

BACKGROUND

Implantable cardioverter defibrillators may be used to deliver high energy cardioversion or defibrillation shocks to a patient's heart when atrial or ventricular tachycardia and/or fibrillation are detected. Cardioversion shocks are typically delivered in synchrony with a detected R-wave when tachycardia and/or fibrillation detection criteria are met. Defibrillation shocks are typically delivered when tachycardia and/or fibrillation criteria are met, and the R-wave cannot be discerned from signals sensed by the ICD.

Currently, ICDs use endocardial or epicardial leads which extend from the ICD housing through the venous system to the heart. Electrodes positioned in or adjacent to the heart by the leads are used for pacing and sensing functions. Cardioversion and defibrillation shocks (e.g., anti-tachyarrhythmia shocks) are generally applied between a coil electrode carried by one of the leads and the ICD housing, which acts as an active can electrode.

In addition, or as an alternative to cardioversion and defibrillation shocks, the ICD or an implantable artificial pacemaker may provide cardiac pacing therapy to the heart when the natural pacemaker and/or conduction system of the heart fails to provide synchronized atrial and ventricular contractions at rates and intervals sufficient to sustain healthy patient function. Such antibradycardial pacing may provide relief from symptoms, or even life support, for a patient. Cardiac pacing may also provide electrical overdrive stimulation (e.g., anti-tachycardia pacing (ATP)) to suppress or convert tachyarrhythmias, again supplying relief from symptoms and preventing or terminating arrhythmias that could lead to sudden cardiac death.

Cardiac pacing by conventional pacemakers and/or ICDs is usually provided by a pulse generator implanted subcutaneously or sub-muscularly in or near a pectoral region of a patient. The generator typically connects to the proximal end of one or more implanted leads, the distal end of which contains one or more electrodes for positioning adjacent to the inside or outside wall of a cardiac chamber. Each of the leads may be secured near or against the cardiac tissue to provide sufficient transmission of electrical energy to the cardiac tissue in order to capture the heart.

SUMMARY

Subcutaneous ICD systems are configured to deliver anti-tachyarrhythmia shock therapy upon detecting certain types of tachyarrhythmias (e.g., ventricular fibrillation (VF)) and some types of ventricular tachycardia (VT)). In certain instances, a patient implanted with a subcutaneous ICD may also have a separate pacemaker device or system implanted, such as a leadless pacing device (LPD), to provide anti-tachycardia pacing (ATP) and/or bradycardia pacing. Since cardiac depolarization waveforms resulting from delivery of pacing pulses, e.g., by the LPD, may have different waveform morphologies than intrinsic cardiac depolarization waveform morphologies, the subcutaneous ICD may incorrectly identify tachyarrhythmia based on misclassifying the paced depolarization waveforms as not normal, e.g., tachyarrhythmic. This disclosure describes techniques for identifying depolarizations of the heart of the patient resulting from pacing by a separate pacemaker device or system as being normal.

The systems, devices, and methods described herein determine one or more paced cardiac depolarization waveform morphological templates for use by an implantable medical device (IMD), such as a subcutaneous ICD, to detect cardiac tachyarrhythmias and/or discriminate between various types of cardiac tachyarrhythmias (e.g., VF vs. VT). More particularly, this disclosure describes techniques that include determining that cardiac depolarizations are paced cardiac depolarizations resulting from delivery of a pacing pulse to the heart by another IMD. The techniques described herein determine that the cardiac depolarizations are paced based on characteristics, such as timing, of cardiac depolarizations, i.e., without detecting the pacing pulse itself, and without communicating with the other IMD that delivers the pacing. After identifying one or more paced cardiac depolarizations, the IMD may determine a paced cardiac depolarization waveform morphological template based on the identified paced cardiac depolarizations.

In some examples, the subcutaneous ICD uses the paced morphological template when performing morphological analysis of a subsequently suspected tachyarrhythmia to expand its classification of what constitutes a normal morphology to include paced cardiac events. In such examples, the subcutaneous ICD may include a plurality of morphology templates (e.g., an intrinsic morphology template and a paced morphology template) and classify cardiac event as normal during morphology analysis when the cardiac event matches any of the plurality of morphology templates.

In some examples, the subcutaneous ICD may additionally or alternatively determine an intrinsic normal cardiac depolarization waveform morphological template based on the paced cardiac depolarization waveform morphological template. In other words, the subcutaneous ICD may verify that various cardiac depolarizations are intrinsic by comparing the waveforms to the paced cardiac depolarization waveform morphological template and determining that the cardiac depolarization waveform is different from the paced cardiac depolarization waveform morphological template. In any example, the subcutaneous ICD may compare the normal cardiac depolarization waveform morphological template or templates (e.g., the intrinsic normal template and, in some examples, the paced normal template) to subsequent cardiac depolarization waveforms. The IMD may detect a cardiac tachyarrhythmia based on the comparison.

In some examples, the IMD is a subcutaneous ICD, and the other IMD is a leadless pacing device (LPD) or other implantable cardiac pacemaker. The subcutaneous ICD may be implanted external to a rib cage of a patient without any leads implanted within the rib cage or within the vasculature. The subcutaneous ICD may also be configured to detect tachyarrhythmias and/or deliver anti-tachyarrhythmia shock therapy (e.g., cardioversion shocks or defibrillation shocks). The LPD may be implanted within a chamber of the heart and include one or more electrodes for monitoring cardiac signals and/or delivering anti-tachycardia pacing therapy, for example.

Use of a paced cardiac depolarization waveform morphological template according to the techniques of this disclosure may allow more accurate morphological detection, discrimination, or confirmation of tachyarrhythmias by an IMD. In some examples, the IMD uses the paced cardiac depolarization waveform morphological template as a normal cardiac depolarization waveform morphological template, which may allow the IMD to avoid detecting a heart rhythm resulting from pacing by another IMD as tachyarrhythmia. In some examples, the IMD uses the paced cardiac depolarization waveform morphological template to more accurately identify intrinsic cardiac depolarizations, by avoiding misidentification of paced depolarizations as being intrinsic depolarizations. More accurately identified intrinsic depolarizations can then be used in generating a normal cardiac depolarization waveform morphological template based on the intrinsic depolarizations. Additionally, an IMD configured according to the techniques of this disclosure may be able to identify the paced depolarizations, resulting from pacing by another device, without detecting the pacing artifact or communicating with the other device.

In one example, the disclosure describes a method that includes sensing, by an implantable medical device, a cardiac electrogram of a heart of a patient, identifying, by the implantable medical device, a plurality of cardiac depolarizations within the cardiac electrogram, and determining, by the implantable medical device, that one or more of the cardiac depolarizations are paced cardiac depolarizations resulting from delivery of a pacing pulse to the heart by another implantable medical device without detecting the pacing pulse and without communicating with the other implantable medical device. The method also includes identifying, by the implantable medical device, one or more paced cardiac depolarization waveforms of the one or more paced cardiac depolarizations. The method further includes determining, by the implantable medical device, a paced cardiac depolarization waveform morphological template based on the one or more identified paced cardiac depolarization waveforms, and determining, by the implantable medical device, a normal cardiac depolarization waveform morphological template based on the paced cardiac depolarization waveform morphological template. The method also includes comparing, by the implantable medical device, the normal cardiac depolarization waveform morphological template to subsequent cardiac depolarization waveforms, and detecting a cardiac tachyarrhythmia based on the comparison of the normal cardiac depolarization waveform morphological template to subsequent cardiac depolarization waveforms.

In another example, the disclosure describes a system comprising a leadless pacing device (LPD) configured to deliver a pacing pulse to a heart of a patient. The system also comprises a subcutaneous implantable cardioverter defibrillator (subcutaneous ICD) configured to sense a cardiac electrogram of the heart, identify a plurality of cardiac depolarizations within the cardiac electrogram, and determine that one or more of the cardiac depolarizations are paced cardiac depolarizations resulting from the delivery of the pacing pulse to the heart by the LPD without detecting the pacing pulse and without communicating with the LPD. The subcutaneous ICD is further configured to identify one or more paced cardiac depolarization waveforms of the one or more paced cardiac depolarizations, determine a paced cardiac depolarization waveform morphological template based on the one or more identified paced cardiac depolarization waveforms, and determine a normal cardiac depolarization waveform morphological template based on the paced cardiac depolarization waveform morphological template. The subcutaneous ICD is further configured to compare the normal cardiac depolarization waveform morphological template to subsequent cardiac depolarization waveforms and detect a cardiac tachyarrhythmia based on the comparison of the normal cardiac depolarization waveform morphological template to subsequent cardiac depolarization waveforms.

In another example, the disclosure describes an implantable medical device (IMD), the IMD comprising a housing configured to be implanted in a patent external to a rib cage of the patient, one or more electrodes configured to be disposed external to the rib cage, and a sensing module configured to sense a cardiac electrogram of a heart of the patient. The IMD further comprises a tachyarrhythmia detection module configured to identify a plurality of cardiac depolarizations within the cardiac electrogram and determine that one or more of the cardiac depolarizations are paced cardiac depolarizations resulting from delivery of a pacing pulse to the heart by another implantable medical device without detecting the pacing pulse and without communicating with the other implantable medical device. The tachyarrhythmia detection module is further configured to identify one or more paced cardiac depolarization waveforms of the one or more paced cardiac depolarizations, determine a paced cardiac depolarization waveform morphological template based on the one or more identified paced cardiac depolarization waveforms, and determine a normal cardiac depolarization waveform morphological template based on the paced cardiac depolarization waveform morphological template. The tachyarrhythmia detection module is further configured to compare the normal cardiac depolarization waveform morphological template to subsequent cardiac depolarization waveforms and detect a cardiac tachyarrhythmia based on the comparison of the normal cardiac depolarization waveform morphological template to subsequent cardiac depolarization waveforms.

In another example, the disclosure is directed to a device comprising means for sensing a cardiac electrogram of a heart of a patient, means for identifying a plurality of cardiac depolarizations within the cardiac electrogram, and means for determining that one or more of the cardiac depolarizations are paced cardiac depolarizations resulting from delivery of a pacing pulse to the heart by another implantable medical device without detecting the pacing pulse and without communicating with the other implantable medical device. The device further comprises means for identifying one or more paced cardiac depolarization waveforms of the one or more paced cardiac depolarizations, means for determining a paced cardiac depolarization waveform morphological template based on the one or more identified paced cardiac depolarization waveforms, and means for determining a normal cardiac depolarization waveform morphological template based on the paced cardiac depolarization waveform morphological template. The device further comprises means for comparing the normal cardiac depolarization waveform morphological template to subsequent cardiac depolarization waveforms and means for detecting a cardiac tachyarrhythmia based on the comparison of the normal cardiac depolarization waveform morphological template to subsequent cardiac depolarization waveforms.

In another example, the disclosure is directed to a non-transitory computer-readable storage medium comprising instructions that, when executed, cause a processor of an implantable medical device to identify a plurality of cardiac depolarizations within a sensed cardiac electrogram of a heart of a patient and determine that one or more of the cardiac depolarizations are paced cardiac depolarizations resulting from delivery of a pacing pulse to the heart by another implantable medical device without detecting the pacing pulse and without communicating with the other implantable medical device. The instructions may further cause the processor to identify one or more paced cardiac depolarization waveforms of the one or more paced cardiac depolarizations, determine a paced cardiac depolarization waveform morphological template based on the one or more identified paced cardiac depolarization waveforms, and determine a normal cardiac depolarization waveform morphological template based on the paced cardiac depolarization waveform morphological template. The instructions may further cause the processor to compare the normal cardiac depolarization waveform morphological template to subsequent cardiac depolarization waveforms and detect a cardiac tachyarrhythmia based on the comparison of the normal cardiac depolarization waveform morphological template to subsequent cardiac depolarization waveforms.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
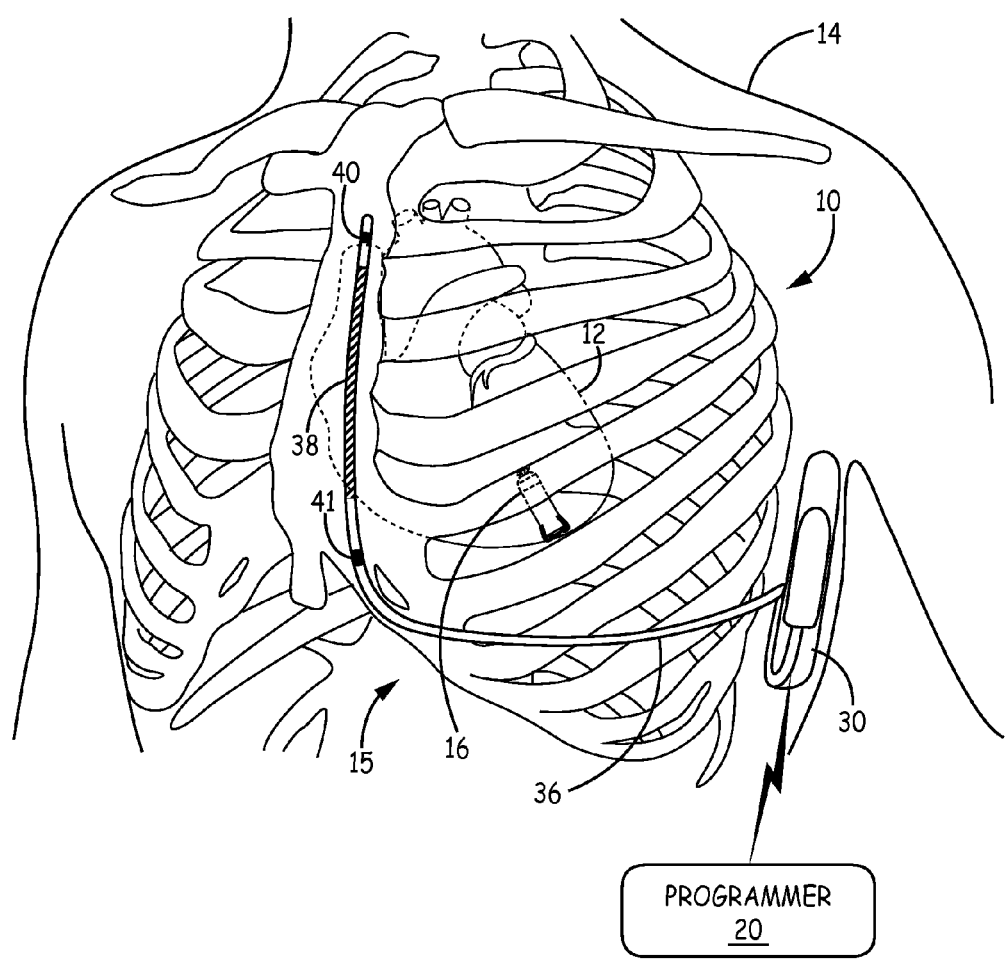
FIG. 1 is a conceptual drawing illustrating an example system that includes a subcutaneous implantable cardioverter defibrillator (subcutaneous ICD) implanted exterior to the rib cage of a patient and a leadless pacing device (LPD) implanted within a cardiac chamber of the patient.

FIG. 1 is a conceptual drawing illustrating an example cardiac system 10 implanted within a patient 14. Cardiac system 10 includes a subcutaneous implantable cardioverter defibrillator (subcutaneous ICD) system 15 implanted above the rib cage and sternum of patient 14 and a leadless cardiac pacing device (LPD) 16 implanted within a heart 12 of patient 14. External programmer 20 may be configured to communicate with one or both of LPD 16 and subcutaneous ICD system 15 via an RF communication link, inductive coupling, or some other wireless communication protocol. Generally, there are no wires or other direct electrical (e.g., hardwired) connections between subcutaneous ICD system 15 and LPD 16, and there is, generally, no communication between subcutaneous ICD system 15 and LPD 16. Patient 14 is ordinarily, but not necessarily, a human patient. As will be described in further detail herein, subcutaneous ICD system 15 is configured to identify paced depolarizations of heart 12 resulting from pacing therapy delivered by LPD 16 by analyzing sensed electrical signals and, in response to detecting the paced depolarizations, modify sensing and/or tachyarrhythmia detection.

Subcutaneous ICD system 15 includes an implantable cardiac defibrillator (ICD) 30 connected to at least one implantable cardiac defibrillation lead 36. Subcutaneous ICD 30 of FIG. 1 is implanted subcutaneously on the left side of patient 14 under the skin but above the ribcage. Defibrillation lead 36 extends subcutaneously under the skin but above the ribcage from subcutaneous ICD 30 toward a center of the torso of patient 14, bends or turns near the center of the torso, and extends subcutaneously superior under the skin but above the ribcage and/or sternum. Defibrillation lead 36 may be offset laterally to the left or the right of the sternum or located over the sternum. Defibrillation lead 36 may extend substantially parallel to the sternum or be angled lateral from the sternum at either the proximal or distal end.

In other instances, lead 36 may be implanted at other extravascular locations. For example, lead 36 may be implanted at least partially in a substernal location, e.g., between the ribcage and/or sternum and heart. In one such configuration, a proximal portion of lead 36 extends subcutaneously from subcutaneous ICD 30 toward the sternum (not seen in the transverse view of FIG. 2) and a distal portion of lead 36 extends superior under or below the sternum in the anterior mediastinum. The anterior mediastinum is bounded laterally by the pleurae, posteriorly by the pericardium, and anteriorly by the sternum. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 36 extends along the posterior side of the sternum substantially within the loose connective tissue and/or substernal musculature of the anterior mediastinum. Lead 36 may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum or ribcage.

Defibrillation lead 36 includes an insulative lead body having a proximal end that includes a connector configured to be connected to subcutaneous ICD 30 and a distal portion that includes one or more electrodes. Defibrillation lead 36 also includes one or more conductors that form an electrically conductive path within the lead body and interconnect the electrical connector and respective ones of the electrodes.

Defibrillation lead 36 includes a defibrillation electrode 38 toward the distal portion of defibrillation lead 36, e.g., toward the portion of defibrillation lead 36 extending along the sternum. Defibrillation lead 36 is placed along sternum such that a therapy vector between defibrillation electrode 38 and a housing electrode formed by or on subcutaneous ICD 30 (or other second electrode of the therapy vector) is substantially across a ventricle of heart 12. The therapy vector may, in one example, be viewed as a line that extends from a point on defibrillation electrode 38 (e.g., a center of the defibrillation electrode 38) to a point on the housing electrode of subcutaneous ICD 30. Defibrillation electrode 38 may, in one example, be an elongated coil electrode.

Defibrillation lead 36 may also include one or more sensing electrodes, such as sensing electrodes 40 and 41, located along the distal portion of defibrillation lead 36. In the example illustrated in FIG. 1, sensing electrodes 40 and 41 are separated from one another by defibrillation electrode 38. In other examples, however, sensing electrodes 40 and 41 may be both distal of defibrillation electrode 38 or both proximal of defibrillation electrode 38. In other examples, lead 36 may include more or fewer electrodes.

ICD system 15 may sense electrical signals via one or more sensing vectors that include combinations of electrodes 40 and 41 and the housing electrode of subcutaneous ICD 30. For example, subcutaneous ICD 30 may obtain electrical signals sensed using a sensing vector between electrodes 40 and 41, obtain electrical signals sensed using a sensing vector between electrode 40 and the conductive housing electrode of subcutaneous ICD 30, obtain electrical signals sensed using a sensing vector between electrode 41 and the conductive housing electrode of subcutaneous ICD 30, or a combination thereof. In some instances, subcutaneous ICD 30 may even sense cardiac electrical signals using a sensing vector that includes defibrillation electrode 38 and one of electrodes 40 and 41 or the housing electrode of subcutaneous ICD 30.

The sensed electrical intrinsic signals may include electrical signals generated by cardiac muscle and indicative of depolarizations and repolarizations of heart 12 at various times during the cardiac cycle. Subcutaneous ICD 30 analyzes the electrical signals sensed by the one or more sensing vectors to detect tachyarrhythmia, such as ventricular tachycardia or ventricular fibrillation. In response to detecting the tachycardia, subcutaneous ICD 30 may begin to charge a storage element, such as a bank of one or more capacitors, and, when charged, deliver one or more defibrillation shocks via defibrillation electrode 38 of defibrillation lead 36 if the tachyarrhythmia is still present and determined to require defibrillation therapy. As will be described in further detail herein, subcutaneous ICD 30 analyzes the sensed electrical signals on lead 36 to identify depolarizations of heart 12 resulting from delivery of pacing therapy by pacing device 16 and, in response to detecting the pacing therapy, modifies the sensing and/or tachyarrhythmia detection to reduce the likelihood that the pacing therapy negatively impacts the sensing and detection of tachyarrhythmias by subcutaneous ICD 30.

As described above, cardiac system 10 also includes at least one cardiac pacing device, such as LPD 16. In the example illustrated in FIG. 1, LPD 16 is an implantable leadless pacing device that provides pacing therapy to heart 12 via a pair of electrodes carried on the housing of pacing device 16. An example cardiac pacing device is described in U.S. patent application Ser. No. 13/756,085 to Greenhut et al., entitled "SYSTEMS AND METHODS FOR LEADLESS PACING AND SHOCK THERAPY," the entire content of which is incorporated herein by reference. Since LPD 16 includes two or more electrodes carried on the exterior its housing, no other leads or structures need to reside in other chambers of heart 12.

In the example of FIG. 1, LPD 16 is implanted within right ventricle of heart 12 to sense electrical activity of heart 12 and deliver pacing therapy, e.g., anti-tachycardia pacing (ATP) therapy, bradycardia pacing therapy, and/or post-shock pacing therapy, to heart 12. Pacing device 16 may be attached to a wall of the right ventricle of heart 12 via one or more fixation elements that penetrate the tissue. These fixation elements may secure pacing device 16 to the cardiac tissue and retain an electrode (e.g., a cathode or an anode) in contact with the cardiac tissue. However, in other examples, system 10 may include additional pacing devices 16 within respective chambers of heart 12 (e.g., right or left atrium and/or left ventricle). In further examples, pacing device 16 may be attached to an external surface of heart 12 (e.g., in contact with the epicardium) such that pacing device 16 is disposed outside of heart 12.

Pacing device 16 may be capable sensing electrical signals using the electrodes carried on the housing of pacing device 16. These electrical signals may be electrical signals generated by cardiac muscle and indicative of depolarizations and repolarizations of heart 12 at various times during the cardiac cycle. Pacing device 16 may analyze the sensed electrical signals to detect tachyarrhythmias, such as ventricular tachycardia or ventricular fibrillation. In response to detecting the tachyarrhythmia, pacing device 16 may, e.g., depending on the type of tachyarrhythmia, begin to deliver ATP therapy via the electrodes of pacing device 16. In addition to or instead of ATP therapy, pacing device 16 may also deliver bradycardia pacing therapy and post-shock pacing therapy.

LPD 16 and subcutaneous ICD system 15 are configured to operate completely independent of one another. In other words, pacing device 16 and subcutaneous ICD system 15 are not capable of establishing telemetry communication sessions with one another to exchange information about sensing and/or therapy using one-way or two-way communication. Instead, each of pacing device 16 and subcutaneous ICD system 15 analyze the data sensed via their respective electrodes to make tachyarrhythmia detection and/or therapy decisions. As such, each device does not know if the other will detect the tachyarrhythmia, if or when it will provide therapy, and the like.

During a tachyarrhythmia that could be treated with either ATP or a defibrillation shock, it is important to ensure that ATP therapies do not overlap or take place after the defibrillation shock. Applying ATP after a defibrillation shock could be pro-arrhythmic and present a hazard to the patient. Moreover, the delivery of the pacing from pacing device 16 could interference with sensing and tachyarrhythmia detection of subcutaneous ICD 30. This interference could take the form of decreased sensitivity (e.g., inability to detect ventricular tachycardia (VT) and/or ventricular fibrillation (VF)) or decreased specificity (e.g., inability to withhold therapy for tachyarrhythmia's determined to not require a defibrillation shock, such as supraventricular tachycardia (SVT), sinus tachycardia (ST), normal sinus rhythm, atrial fibrillation, atrial flutter, or the like). Systems could be designed to provide device-to-device communication between subcutaneous ICD system 15 and pacing device 16, but this may add complexity to the system and not be highly effective or fast enough to prevent unwanted ATP therapies post defibrillation shock. The techniques described herein reduce and, in some cases, eliminate the interference with sensing and tachyarrhythmia detection of subcutaneous ICD 30.

This disclosure describes various techniques for determining paced cardiac depolarization waveform morphological templates that may be implemented by an IMD, such as subcutaneous ICD 30, another ICD, or other device that detects or discriminates cardiac arrhythmias. Typically, an ICD, such as subcutaneous ICD 30 as an example, may be configured to detect tachyarrhythmias and deliver anti-tachyarrhythmia shock therapy. The ICD detects these tachyarrhythmias by creating a normal waveform morphological template of a patient's heartbeat, and comparing subsequent cardiac depolarization waveforms to the waveform morphological template. If the subsequent cardiac depolarization waveforms are different from the normal waveform morphological template, then the ICD may determine that a tachyarrhythmia is occurring and administer anti-tachyarrhythmia shock therapy.

This process can go awry when a patient is further outfitted with a separate cardiac pacemaker, such as a LPD 16, which may occur when a patient is both prone to tachyarrhythmia and requires bradycardia pacing support. An issue may arise when the ICD is not in communication with the LPD, such as when subcutaneous ICD 30 and LPD 16 are configured for independent operation. In particular, when the pacemaker delivers a pacing signal, it causes a cardiac depolarization waveform that is morphologically different than a cardiac depolarization waveform resulting from an intrinsic depolarization.

ICDs are configured to deliver anti-tachyarrhythmia shock therapy upon detecting a tachyarrhythmia, which may include detecting one or more cardiac depolarization waveforms that looks different from a normal cardiac depolarization waveform morphological template. Since a cardiac depolarization waveform resulting from delivery of a pacing pulse, e.g., by LPD 16, looks different from an intrinsic cardiac depolarization waveform morphological template, the ICD may incorrectly identify tachyarrhythmia based on misclassifying paced depolarization waveforms as not normal, e.g., tachyarrhythmic. An example of a paced depolarization waveform can be seen with respect to FIG. 8, described below. Furthermore, if the ICD incorrectly identifies a paced cardiac depolarization waveform as being intrinsic and usable for generation of a normal morphological template, instead of an intrinsic depolarization, the ICD may incorrectly identify intrinsic cardiac depolarizations as tachyarrhythmic. Further, ICDs and pacemakers must run on battery power. Enabling communication between an ICD and an LPD whenever the LPD is in use would be harmful to the battery life of both devices.

According to techniques of this disclosure, a normal cardiac depolarization waveform morphological template may be any template that an ICD, such as subcutaneous ICD 30, uses to determine whether a tachyarrhythmia is occurring. In the examples provided herein, subcutaneous ICD 30 may store a single type of normal cardiac depolarization waveform morphological template, e.g., an intrinsic normal morphological template, or both types of normal cardiac depolarization waveform morphological templates, i.e., both an intrinsic normal morphological template and a paced normal morphological template. In either case, subcutaneous ICD 30 may determine the normal cardiac depolarization waveform morphological template(s) based on a paced cardiac depolarization waveform morphological template.

For example, subcutaneous ICD 30 may use a paced cardiac depolarization waveform morphological template as a paced normal waveform morphological template. In the case of an intrinsic normal waveform morphological template, subcutaneous ICD 30 may determine the intrinsic normal template by comparing cardiac depolarizations to the paced cardiac depolarization waveform morphological template. If a cardiac depolarization matches the paced cardiac depolarization waveform morphological template, then subcutaneous ICD 30 may discard the cardiac depolarization. If the cardiac depolarization does not match the paced cardiac depolarization waveform morphological template, then subcutaneous ICD use the cardiac depolarization as a candidate for determining the normal cardiac depolarization waveform morphological template.

Therefore, this disclosure describes techniques for determining paced cardiac depolarization waveform morphological templates that may be implemented by an IMD, such as subcutaneous ICD 30. This may allow, for example, subcutaneous ICD 30 to detect when cardiac depolarization waveforms are the result of pacing by another IMD, such as LPD 16, without having to directly communicate the LPD or detect the pacing pulses themselves. This may prevent subcutaneous ICD 30 from inappropriately detecting a tachyarrhythmia that requires therapy (e.g., detecting a false positive) and wrongly issuing anti-tachyarrhythmia shock therapy. Providing this capability without subcutaneous ICD 30 and LPD 16 being in direct communication with one another further optimizes the resources (e.g., battery capacity or processing power) available to each device.

In accordance with techniques of this disclosure, subcutaneous ICD 30 may be configured to determine whether depolarizations of heart 12 are the result of pacing signals provided to heart 12 by LPD 16 based on a paced cardiac depolarization waveform morphological template generated during a period of time in which the depolarizations of heart 12 are caused by pacing. Subcutaneous ICD 30 may determine that one or more of the cardiac depolarizations are paced cardiac depolarizations using various techniques, examples of which are described below with respect to FIG. 4. Subcutaneous ICD 30 may determine a paced cardiac depolarization waveform morphological template based on one or more identified paced cardiac depolarization waveforms. Examples of methods for generating a template for a known cardiac rhythm are generally described in U.S. Pat. No. 7,062,315 (Koyrakh, et al.) and U.S. Pat. No. 7,242,978 (Cao, et al.), both patents incorporated herein by reference in their entirety. For example, templates may be generated by computing cross matches between any paced cardiac depolarization waveforms that are identified from the one or more paced cardiac depolarizations identified above. If the cross matches are similar enough, such as whether they are within a threshold, a template may be generated from the cross matches.

Although the techniques disclosed herein are described in the context of the example cardiac system 10 illustrated in FIG. 1, which includes subcutaneous ICD system 15 and leadless pacing device 16, the techniques may be applicable to other coexistent systems. For example, instead of a leadless pacing device, a pacing system may be implanted having a pacemaker and one or more leads connected to and extending from the pacemaker into one or more chambers of the heart or attached to the outside of the heart to provide pacing therapy to the one or more chambers. As such, the example of FIG. 1 is illustrated for exemplary purposes only and should not be considered limiting of the techniques described herein.

External programmer 20 may be configured to communicate with one or both of subcutaneous ICD 30 and LPD 16.

In some examples, programmer 20 comprises a handheld computing device, computer workstation, or networked computing device. Programmer 20 may include a user interface that receives input from a user. In other examples, the user may also interact with programmer 20 remotely via a networked computing device. The user may interact with programmer 20 to communicate with LPD 16 and/or subcutaneous ICD 30. For example, the user may interact with programmer 20 to send an interrogation request and retrieve therapy delivery data, update therapy parameters that define therapy, manage communication between LPD 16 and/or subcutaneous ICD 30, or perform any other activities with respect to LPD 16 and/or subcutaneous ICD 30. In some examples, programmer 20 may be configured to perform some or all of the techniques described herein, e.g., determined waveform templates for used by subcutaneous ICD 30 based on electrograms received from subcutaneous ICD 30. Although the user is a physician, technician, surgeon, electrophysiologist, or other healthcare professional, the user may be patient 14 in some examples.

Programmer 20 may communication with LPD 16 and/or subcutaneous ICD 30 via wireless communication using any techniques known in the art. Examples of communication techniques may include, for example, radiofrequency (RF) telemetry, but other techniques are also contemplated. In some examples, programmer 20 may include a programming head that may be placed proximate to the patient's body near the LPD 16 and/or subcutaneous ICD 30 implant site in order to improve the quality or security of communication between LPD 16 and/or subcutaneous ICD 30 and programmer 20.

Figure 2:
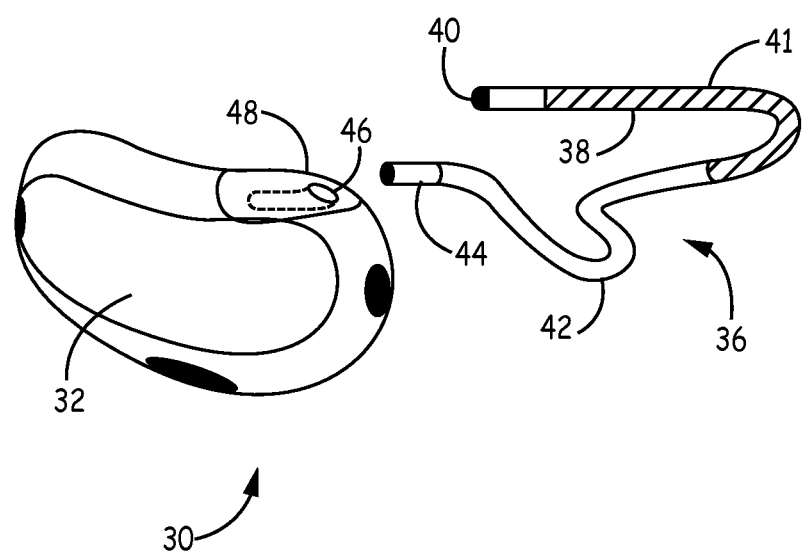
FIG. 2 is a conceptual drawing illustrating different views of the example subcutaneous ICD of FIG. 1

FIG. 2 is a conceptual drawing illustrating subcutaneous ICD system 15 of FIG. 1. In the example of FIG. 2, housing 32 of subcutaneous ICD 30 may be constructed as an ovoid with a substantially kidney-shaped profile. The ovoid shape of housing 32 may promote ease of subcutaneous implantation and may minimize patient discomfort during normal body movement and flexing of the thoracic musculature. In other examples, housing 32 may be constructed with different shapes intended for different implant locations and/or to house different components, subcutaneous leads, or configurations for electrodes in FIG. 2.

Housing 32 may contain the electronic circuitry of subcutaneous ICD 30. Header 48 and connector 46 may provide an electrical connection between distal electrode coil 38 and sensing electrodes 40, 41 of lead 36 and the circuitry within housing 32. Subcutaneous lead 36 may include distal defibrillation coil electrode 38, distal sensing electrode 40, proximal sensing electrode 41, insulated flexible lead body 42, and proximal connector pin 44.

In some examples, housing 32 may be configured as an electrically conductive surface and operate as an electrode. Housing 32 may be referred to as a "can electrode" or used as an indifferent electrode. In some examples, housing 32 may be used as an electrode with coil electrode 38 during delivery of an anti-tachyarrhythmia shock.

In other examples, housing 32 may be coupled to a second subcutaneous lead extending away from housing 32 in the opposite direction of lead 36. In this manner, the second subcutaneous lead may carry one or more of electrodes. Housing 32 may alternatively be coupled to three or more subcutaneous leads. In other examples, lead 36 may be formed as an extension of housing 32 such that subcutaneous ICD 30 comprises an elongated housing to carry electrodes.

Figure 3:
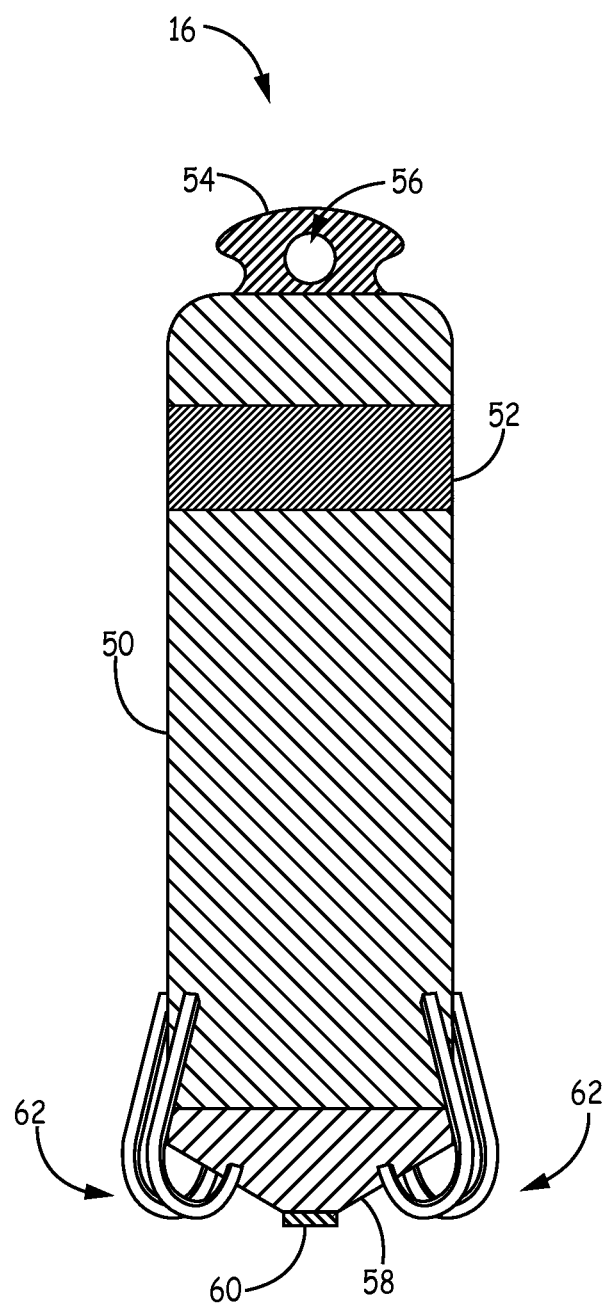
FIG. 3 is a conceptual drawing illustrating the example LPD of FIG. 1.

FIG. 3 is a conceptual drawing illustrating LPD 16 of FIG. 1. As shown in FIG. 3, LPD 16 includes case 50, cap 58, electrode 60, electrode 52, fixation mechanisms 62, flange 54, and opening 56. Together, case 50 and cap 58 may be considered the housing of LPD 16. In this manner, case 50 and cap 58 may enclose and protect the various electrical components within LPD 16. Case 50 may enclose substantially all of the electrical components, and cap 58 may seal case 50 and create the hermetically sealed housing of LPD 16.

Electrodes 52 and 60 are carried on the housing created by case 50 and cap 58. In this manner, electrodes 52 and 60 may be considered leadless electrodes. In the example of FIG. 3, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode and electrode 52 may be used as an anode, or vice versa, for delivering pacing stimulation therapy such as bradycardia pacing, ATP, or post-shock pacing. In addition, LPD 16 may use electrodes 52 and 60 to detect intrinsic electrical signals from cardiac muscle. In other examples, LPD 16 may include three or more electrodes, where each electrode may deliver therapy and/or detect intrinsic signals.

Fixation mechanisms 62 may attach LPD 16 to cardiac tissue. Fixation mechanisms 62 may be active fixation tines, screws, clamps, adhesive members, or any other types of attaching a device to tissue. As shown in the example of FIG. 3, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of LPD 16. For example, a suture or other device may be inserted around flange 54 and/or through opening 56 and attached to tissue. In this manner, flange 54 may provide a secondary attachment structure to tether or retain LPD 16 within heart 12 if fixation mechanisms 62 fail. Flange 54 and/or opening 56 may also be used to extract LPD 16 once the LPD needs to be explanted (or removed) from patient 14 if such action is deemed necessary.

Figure 4:
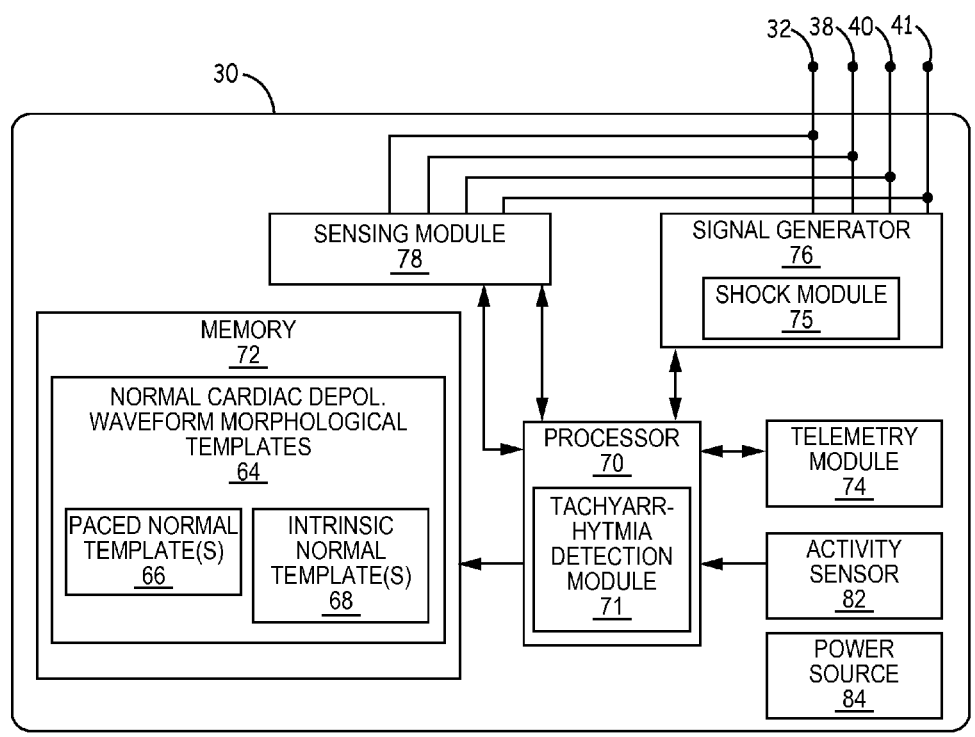
FIG. 4 is a functional block diagram illustrating an example configuration of the subcutaneous ICD of FIG. 1.

FIG. 4 is a functional block diagram illustrating an example configuration of subcutaneous ICD 30 of FIG. 1. In the illustrated example, subcutaneous ICD 30 includes a processor 70, memory 72, shock module 75, signal generator 76, sensing module 78, telemetry module 74, communication module 80, activity sensor 82, and power source 84. Memory 72 includes computer-readable instructions that, when executed by processor 70, cause subcutaneous ICD 30 and processor 70 to perform various functions attributed to subcutaneous ICD 30 and processor 70 herein (e.g., detection of tachyarrhythmias, communication with LPD 16, and/or delivery of anti-tachyarrhythmia shock therapy). Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Processor 70 controls signal generator 76 to deliver stimulation therapy to heart 12 according to a therapy parameters, which may be stored in memory 72. For example, processor 70 may control signal generator 76 to deliver electrical pulses (e.g., shock pulses) with the amplitudes, pulse widths, frequency, or electrode polarities specified by the therapy parameters. In this manner, signal generator 76 may deliver electrical pulses to heart 12 via electrodes 32 (a housing or can electrode), 38, 40, and/or 41. Subcutaneous ICD 30 may use any combination of electrodes to deliver anti-tachycardia therapy and/or detect electrical signals from patient 14. However, in general, coil electrode 38 may be used to deliver an anti-tachyarrhythmia shock.

Signal generator 76 may also include shock module 75. Shock module 75 may include circuitry and/or capacitors required to deliver an anti-tachyarrhythmia shock. For example, signal generator 76 may charge shock module 75 to prepare for delivering a shock. Shock module 75 may then discharge to enable signal generator 76 to deliver the shock to patient 14 via one or more electrodes. In other examples, shock module 75 may be located within subcutaneous ICD 30 but outside of signal generator 76.

Signal generator 76 is electrically coupled to electrodes 32, 38, 40, and 41. In the illustrated example, signal generator 76 is configured to generate and deliver electrical anti-tachyarrhythmia shock therapy to heart 12. For example, signal generator 76 may, using shock module 75, deliver shocks to heart 12 via a subset of electrodes 32, 38, 40, and 41, such as coil electrode 38 and housing or can electrode 32. In some examples, signal generator 76 may deliver pacing stimulation, and cardioversion or defibrillation shocks in the form of electrical pulses. In other examples, signal generator may deliver one or more of these types of stimulation or shocks in the form of other signals, such as sine waves, square waves, or other substantially continuous time signals.

Signal generator 76 may include a switch module, and processor 70 may use the switch module to select, e.g., via a data/address bus, which of the available electrodes are used to deliver shock and/or pacing pulses, and the polarities of the electrodes. The switch module may include a switch array, switch matrix, multiplexer, or any other type of switching device suitable to selectively couple stimulation energy to selected electrodes.

Electrical sensing module 78 may be configured to monitor signals from at least one of electrodes 32, 38, 40, and 41 in order to monitor electrical activity of heart 12, impedance, or other electrical phenomenon. For example, electrical sensing module 78 may monitor electrical activity of heart 12 via sensing electrodes 40 and 41. Sensing may be done to determine heart rates or heart rate variability, or to detect arrhythmias (e.g., tachyarrhythmia). Sensing module 78 may also include a switch module to select which of the available electrodes are used to sense the heart activity, depending upon which electrode combination, or electrode vector, is used in the current sensing configuration. In examples with several electrodes, processor 70 may select the electrodes that function as sense electrodes, i.e., select the sensing configuration, via the switch module within sensing module 78. Sensing module 78 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 70, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 70 may control the functionality of sensing module 78 by providing signals via a data/address bus.

Processor 70 may include a timing and control module, which may be embodied as hardware, firmware, software, or any combination thereof The timing and control module may comprise a dedicated hardware circuit, such as an ASIC, separate from other processor 70 components, such as a microprocessor, or a software module executed by a component of processor 70, which may be a microprocessor or ASIC. The timing and control module may implement programmable counters.

Interval counters implemented by the timing and control module of processor 70 may be reset upon sensing of R-waves and P-waves with detection channels of sensing module 78. The value of the count present in the interval counters when reset by sensed R-waves and P-waves may be used by processor 70 to measure the durations of R-R intervals, P-P intervals, P-R intervals and R-P intervals, which are measurements that may be stored in memory 72. Processor 70 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 72 may be configured as a plurality of recirculating buffers, capable of holding series of measured intervals, which may be analyzed by processor 70 in response to the occurrence of a pace or sense interrupt to determine whether the patient's heart 12 is presently exhibiting atrial or ventricular tachyarrhythmia.

In some examples, processor 70 may determine that tachyarrhythmia has occurred by identification of shortened R-R (or P-P) interval lengths. Generally, processor 70 detects tachycardia when the interval length falls below 220 milliseconds (ms) and fibrillation when the interval length falls below 180 ms. In other examples, processor 70 may detect ventricular tachycardia when the interval length falls between 330 ms and ventricular fibrillation when the interval length falls between 240 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples. In addition to detecting and identifying specific types of cardiac rhythms (types of cardiac events), sensing module 78 may also sample the detected intrinsic signals to generate an electrogram or other time-based indication of cardiac events.

Memory 72 may be configured to store a variety of operational parameters, therapy parameters, sensed and detected data, and any other information related to the monitoring, therapy and treatment of patient 14. Memory 72 may store, for example, thresholds and parameters indicative of tachyarrhythmias and/or therapy parameter values that at least partially define delivered anti-tachyarrhythmia shocks.

Memory 72 may also be configured to store the various morphological templates described herein, such as the paced cardiac depolarization waveform morphological template, the normal cardiac depolarization waveform morphological template, and the intrinsic cardiac depolarization waveform morphological template. Furthermore, memory 72 may be configured to store the depolarization waveforms, e.g., portions of the cardiac electrogram, used to generate such templates, as well as instructions and parameters for generation of the templates based on one or more such waveforms.

Activity sensor 82 may be contained within the housing of subcutaneous ICD 30 and include one or more accelerometers or other devices capable of detecting motion and/or position of subcutaneous ICD 30. For example, activity sensor 82 may include a 3-axis accelerometer that is configured to detect accelerations in any direction in space. Accelerations detected by activity sensor 82 may be used by processor 70 to identify potential noise in signals detected by sensing module 78 and/or confirm the detection of arrhythmias or other patient conditions.

Telemetry module 74 includes any suitable hardware, firmware, software or any combination thereof for communicating with another device, such as programmer 20 (FIG. 1). As described herein, telemetry module 74 may transmit generated or received arrhythmia data, therapy parameter values, communications between subcutaneous ICD 30 and LPD 16, or any other information. For example, telemetry module 74 may transmit information representative of sensed physiological data such as R-R intervals or any other data that may be used by LPD 16 to determine a condition of patient 14. Telemetry module 74 may also be used to receive updated therapy parameters from programmer 20. Under the control of processor 70, telemetry module 74 may receive downlink telemetry from and send uplink telemetry to programmer 20 with the aid of an antenna, which may be internal and/or external. Processor 70 may provide the data to be uplinked to programmer 20 and the control signals for the telemetry circuit within telemetry module 74, e.g., via an address/data bus. In some examples, telemetry module 74 may provide received data to processor 70 via a multiplexer.

In some examples, subcutaneous ICD 30 may signal programmer 20 to further communicate with and pass the alert through a network such as the Medtronic CareLink® Network developed by Medtronic, Inc., of Minneapolis, Minn., or some other network linking patient 14 to a clinician. Subcutaneous ICD 30 may spontaneously transmit the diagnostic information to the network or in response to an interrogation request from a user.

Power source 84 may be any type of device that is configured to hold a charge to operate the circuitry of subcutaneous ICD. Power source 84 may be provided as a rechargeable or non-rechargeable battery. In other examples, power source 84 may also incorporate an energy scavenging system that stores electrical energy from movement of subcutaneous ICD 30 within patient 14.

In accordance with techniques of this disclosure, components of subcutaneous ICD 30 may be configured to determine whether cardiac depolarizations are the result of pacing by another IMD, e.g., LPD 16, and determine a paced cardiac waveform morphological template based on paced depolarization. Subcutaneous ICD 30 may use the paced cardiac waveform morphological template as one type of normal template, referred to as a paced normal template, for morphological detection of tachyarrhythmias. Another type of normal template is an intrinsic normal template. Subcutaneous ICD 30 may use an intrinsic normal template to discriminate between non-treatable intrinsic rhythms and treatable intrinsic tachyarrhythmia. Subcutaneous ICD 30 may use a paced normal template to avoid characterizing a paced cardiac rhythm, which may morphological dissimilar to the intrinsic normal template, as a treatable tachyarrhythmia.

In some examples, subcutaneous ICD 30 may use the paced cardiac waveform morphological template in determining the intrinsic normal morphological template for tachyarrhythmia detection. In particular, subcutaneous ICD 30 may use the paced cardiac waveform morphological template to discriminate between paced and intrinsic waveforms such that intrinsic waveforms, and not paced waveforms, are used to construct the intrinsic normal template for subsequent tachyarrhythmia detection. Subcutaneous ICD 30 may use the paced cardiac waveform morphological template in determining the intrinsic normal morphological template in both examples in which the paced cardiac waveform morphological template is also used as the paced normal template, as well as example in which the ICD does not use a paced normal template for detection of tachyarrhythmias.

Processor 70 of subcutaneous ICD 30 may comprise tachyarrhythmia detection module 71 that may be configured to execute one or more techniques of this disclosure. In some examples, tachyarrhythmia detection module 71 may determine a heart rate for heart 12 of patient 14, e.g., based on intervals between R-waves detected by sensing module 78, as discussed above. Subcutaneous ICD 30 may then determine if the heart rate is a heart rate where it is possible that LPD 16 may be in use.

Tachyarrhythmia detection module 71 of subcutaneous ICD 30 may be configured to determine that one or more of the cardiac depolarizations are paced cardiac depolarizations resulting from delivery of a pacing pulse to heart 12 by LPD 16 without detecting the pacing pulse and without communicating with LPD 16. Tachyarrhythmia detection module 71 of subcutaneous ICD 30 may determine that one or more of the cardiac depolarizations are paced cardiac depolarizations through various tactics. In some examples, tachyarrhythmia detection module 71 of subcutaneous ICD 30 may receive user input, e.g., via programmer 20, that indicates one or more cardiac depolarizations of the plurality of cardiac depolarizations that are paced cardiac depolarizations. In another example, tachyarrhythmia detection module 71 of subcutaneous ICD 30 may compare each of the plurality of cardiac depolarizations to a stored default paced cardiac depolarization model.

In other examples, tachyarrhythmia detection module 71 may detect a first series of cardiac depolarizations of the plurality of cardiac depolarizations with a first set of beat characteristics. In this example, tachyarrhythmia detection module 71 may further detect a second series of cardiac depolarizations of the plurality of cardiac depolarizations subsequent to the first series of cardiac depolarizations with a second set of beat characteristics different than the first set of beat characteristics. Tachyarrhythmia detection module 71 may also detect a third series of cardiac depolarizations of the plurality of cardiac depolarizations subsequent to the second series of cardiac depolarizations with a third set of beat characteristics that are the same as the first set of beat characteristics. Tachyarrhythmia detection module 71 may determine that the first series of cardiac depolarizations and the third series of cardiac depolarizations are paced cardiac depolarizations resulting from delivery of the pacing pulse to the heart by LPD 16 without detecting the pacing pulse and without communicating with LPD 16.

In some examples of this technique, the first set of beat characteristics may comprise a sudden change in ventricular heart rate by a consistent amount over a short run set of beats with morphology stabilizing to a consistent form for the final two beats. In some examples, the short run set of beats may be four beats. The second series of beats are identified by a pause and re-emergence of the pre-elevation heart rate with consistent morphology after the second pre-elevation rate beat. The third series of depolarizations are identified by a similar or greater increase in heart rate to the first series, again with establishment of a stable morphology after a small number of depolarizations at the elevated rate.

Tachyarrhythmia detection module 71 may identify the one or more paced cardiac depolarization waveforms of the final two cardiac depolarizations in the first series of cardiac depolarizations, or the final two cardiac depolarizations in the third series of cardiac depolarizations, as examples, as paced cardiac depolarizations for use in generating a paced cardiac depolarization waveform template. In other examples, tachyarrhythmia detection module 71 may identify the one or more paced cardiac depolarization waveforms of the final cardiac depolarization in the first series of cardiac depolarizations or the final cardiac depolarization in the third series of cardiac depolarizations, as paced cardiac depolarizations for use in generating a paced cardiac depolarization waveform template. In general, tachyarrhythmia detection module 71 may identify the one or more paced cardiac depolarization waveforms of the final N cardiac depolarization in the first series of cardiac depolarizations or the final N cardiac depolarization in the third series of cardiac depolarizations, where N is some number of cardiac depolarizations.

In some examples, tachyarrhythmia detection module 71 first determines a heart rate for each of the plurality of cardiac depolarizations and uses various characteristics of the heart rate to determine that the cardiac depolarizations are paced cardiac depolarizations. In one example, tachyarrhythmia detection module 71 may compare the heart rate for each of the plurality of cardiac depolarizations to a rate floor. The rate floor, in some examples, may be the slowest possible heart rate at which a pacemaker, e.g., LPD 16 is programmed to pace the heart, e.g., 60 beats-per-minute. In other examples, the rate floor may be any heart rate above the slowest heart rate. In these examples, tachyarrhythmia detection module 71 may, for each cardiac depolarization that has a heart rate within a pre-determined range of the rate floor, determine that the cardiac depolarization is a paced cardiac depolarization resulting from delivery of the pacing pulse to the heart by LPD 16 without detecting the pacing pulse and without communicating with LPD 16.

In some examples, the rate floor may be a modulated rate floor, e.g., may be modulated based on activity. In some examples, Tachyarrhythmia detection module 71 may determine an activity level of the patient. For example, tachyarrhythmia detection module 71 may receive information from activity sensor 82 and determine a rate floor based on the level of activity detected in activity sensor 82. For instance, if activity sensor 82 is detecting a high amount of activity, the modulated rate floor may be relatively higher. Alternatively, if activity sensor 82 is detecting a low amount of activity, the modulated rate floor may be relatively lower. In another example, instead of or in addition to activity measured by activity sensor 82, tachyarrhythmia detection module may determine a modulated rate floor based on previously measured heart rates.

In another example, tachyarrhythmia detection module 71 may detect a large increase in the heart rate between a first pair of consecutive cardiac depolarizations. In this example, tachyarrhythmia detection module 71 may further detect a plurality of small decreases in the heart rate between a plurality of pairs of consecutive cardiac depolarizations subsequent to the first pair of consecutive cardiac depolarizations. For example, the heart rate may start as an irregular rapid heartbeat around 95 beats per minute (bpm). Tachyarrhythmia detection module 71 may detect a large increase in the heart rate, such as an increase as large as 50 bpm, followed by a series of small, stable decreases thereafter. This may be an indication that the increase followed by the plurality of decreases is due to activity from LPD 16. Alternatively, if the pattern is irregular or unstable, it may be an arrhythmia. Tachyarrhythmia detection module 71 may then, for at least one cardiac depolarization in the plurality of cardiac depolarizations subsequent to the pair of cardiac depolarizations, determine that the cardiac depolarization is a paced cardiac depolarization resulting from delivery of the pacing pulse to the heart by LPD 16 without detecting the pacing pulse and without communicating with LPD 16.

In still another example, tachyarrhythmia detection module 71 may detect a patterned decrease in the heart rate amongst a subset of the plurality of cardiac depolarizations, such as a smooth rate decrease of the heart rates or a plurality of decreases by a discrete number of the heart rates. If the patterned decrease is sustained for a duration of time across the plurality of cardiac depolarizations, then it may be an indication that LPD 16 is sending pacing pulses to heart 12. In this example, tachyarrhythmia detection module 71 of subcutaneous ICD 30 may, for at least one cardiac depolarization in the subset of cardiac depolarizations, determine that the cardiac depolarization is a paced cardiac depolarization resulting from delivery of the pacing pulse to the heart by LPD 16 without detecting the pacing pulse and without communicating with LPD 16.

In yet another example, tachyarrhythmia detection module 71 of subcutaneous ICD 30 may detect a series of modulations in the heart rate amongst a subset of the plurality of cardiac depolarizations, wherein the series of modulations comprises an increase by a specific number of beats per minute followed by a decrease by the same specific number of beats per minute. This may occur in an instance where patient 14 has a respiratory sinus arrhythmia, where LPD 16 may send pacing pules such that the heart rate of patient 14 may cycle back and form with a modulation of about 5 bpm. In this example, tachyarrhythmia detection module 71 may, for at least one cardiac depolarization in the subset of cardiac depolarizations, determine that the cardiac depolarization is a paced cardiac depolarization resulting from delivery of the pacing pulse to the heart by LPD 16 without detecting the pacing pulse and without communicating with LPD 16.

In still another example, the cardiac depolarizations may comprise ventricular depolarizations, and atrial depolarizations may further be detected, e.g., by sensing module 78 via electrodes 40 and 41. Tachyarrhythmia detection module 71 may identify an atrio-ventricular block based on the atrial depolarizations and the ventricular depolarizations. In this example, in response to identifying the atrio-ventricular block, tachyarrhythmia detection module 71 may determine that at least one of the ventricular depolarizations during the atrio-ventricular block is a paced cardiac depolarization resulting from delivery of the pacing pulse to the heart by the other implantable medical device without detecting the pacing pulse and without communicating with the other implantable medical device.

One example of this technique may be tachyarrhythmia detection module 71 identifying paced depolarizations as depolarizations during a high atrial rate in which a sudden decrease in ventricular rate to one-half the atrial rate is measured with a small elevation in the atrial rate, such as an elevation of around 5 bpm. The paced depolarizations may be identified by a comparison of an end depolarization of the rapid ventricular rate to the first depolarization of the detected half-rate period. Matching those depolarizations may indicate modulation of the pacing rate by upper rate limits of LPD 16. Distinctions between atrial and ventricular depolarizations can be determined by length and amplitude of the respective depolarizations. For example, atrial depolarizations tend to have a lower amplitude over a longer period, while ventricular depolarizations tend to have a larger amplitude over a shorter period.

Once tachyarrhythmia detection module 71 determines that certain conditions are met that indicate heart 12 may be beating with the assistance of LPD 16 and identifies one or more paced cardiac depolarizations, e.g., using any one or more of the above-described techniques, tachyarrhythmia detection module 71 may create a morphological template of the paced cardiac depolarizations. To accomplish this, tachyarrhythmia detection module 71 of subcutaneous ICD 30 may be further configured to identify one or more paced cardiac depolarization waveforms of the one or more paced cardiac depolarizations. A paced cardiac depolarization waveform may be a portion of the cardiac electrogram associated with the depolarization, which is sampled and stored as the paced cardiac depolarization waveform. Tachyarrhythmia detection module 71 may determine a paced cardiac depolarization waveform morphological template based on the one or more identified paced cardiac depolarization waveforms.

Examples of methods for generating a template for a known cardiac rhythm are generally described in U.S. Pat. No. 7,062,315 (Koyrakh, et al.) and U.S. Pat. No. 7,242,978 (Cao, et al.), both patents incorporated herein by reference in their entirety. For example, templates may be generated by computing cross matches between any paced cardiac depolarization waveforms that are identified from the one or more paced cardiac depolarizations identified above. If the cross matches are similar enough, such as whether they are within a threshold, a template may be generated from the cross matches.

In some examples, based on the paced cardiac depolarization waveform morphological template, tachyarrhythmia detection module 71 of subcutaneous ICD 30 may determine a normal cardiac depolarization waveform morphological template. In particular, tachyarrhythmia detection module 71 may use the determined paced cardiac depolarization waveform morphological template as a paced normal template, in addition to an intrinsic normal template, for tachyarrhythmia detection. Using a paced normal template, tachyarrhythmia detection module 71 may avoid detecting tachyarrhythmia based on paced cardiac depolarizations.

In some examples, tachyarrhythmia detection module 71 of subcutaneous ICD 30 may identify true intrinsic cardiac depolarization waveforms based on the paced cardiac depolarization waveform morphological template, i.e., may avoid misclassifying paced depolarizations as intrinsic, and using the misidentified paced depolarizations to generate an intrinsic normal template for tachyarrhythmia detection. In examples where tachyarrhythmia detection module 71 identified intrinsic cardiac depolarization waveforms using the paced cardiac depolarization waveform morphological template, tachyarrhythmia detection module 71 may determine the intrinsic normal cardiac depolarization waveform morphological template based on the identified intrinsic cardiac depolarization waveforms. Because the paced cardiac depolarization waveform morphological template was used to identify intrinsic depolarization waveforms for generation of the intrinsic normal template, tachyarrhythmia detection module 71 may be considered to have generated the intrinsic normal template for subsequent tachyarrhythmia detection based on the paced cardiac depolarization waveform morphological template.

Using one or more normal cardiac depolarization waveform morphological templates, e.g., an intrinsic normal template, or an intrinsic normal template and a paced normal template, tachyarrhythmia detection module 71 may be able to determine whether future heartbeats of heart 12 are actually the result of tachyarrhythmia, e.g., a treatable tachyarrhythmia. For instance, tachyarrhythmia detection module 71 may be configured to compare the one or more normal cardiac depolarization waveform morphological templates to subsequent cardiac depolarization waveforms. Further, tachyarrhythmia detection module 71 may be configured to detect a cardiac tachyarrhythmia based on the comparison of the one or more normal cardiac depolarization waveform morphological templates to subsequent cardiac depolarization waveforms.

In some examples, tachyarrhythmia detection module 71 may develop or generate an intrinsic normal cardiac depolarization waveform morphological template based on intrinsic or natural heartbeats. An intrinsic normal cardiac depolarization waveform morphological template may allow tachyarrhythmia detection module 71 to avoid classifying intrinsic cardiac depolarizations as tachyarrhythmias. In some examples, tachyarrhythmia detection module 71 may identify an intrinsic cardiac depolarization waveform based on a comparison of a depolarization waveform to the paced cardiac depolarization waveform morphological template to determine that the identified depolarization was intrinsic rather than paced, and determine the intrinsic normal cardiac depolarization waveform morphological template based on the identified intrinsic cardiac depolarization waveform.

In some examples, tachyarrhythmia detection module 71 may determine a second, paced normal cardiac depolarization waveform morphological template based on paced cardiac depolarizations. In such examples, tachyarrhythmia detection module 71 may use the paced cardiac depolarization waveform morphological template as a paced normal template for tachyarrhythmia detection. Tachyarrhythmia detection module 71 may then compare the first, intrinsic normal cardiac depolarization waveform morphological template and the second, paced normal cardiac depolarization waveform morphological template to subsequent cardiac depolarization waveforms and detect a cardiac tachyarrhythmia based on the comparison of the first normal cardiac depolarization waveform morphological template and the second normal cardiac depolarization waveform morphological template to subsequent cardiac depolarization waveforms.

In some examples, tachyarrhythmia detection module 71 may update the one or more normal cardiac depolarization waveform morphological templates. In such examples, sensing module 78 may sense a second cardiac electrogram of the heart of the patient. Tachyarrhythmia detection module 71 30 may identify a second plurality of cardiac depolarizations within the second cardiac electrogram, and determine that one or more of the second cardiac depolarizations are second paced cardiac depolarizations resulting from delivery of a second pacing pulse to the heart by LPD 16 without detecting the pacing pulse and without communicating with LPD 16. Tachyarrhythmia detection module 71 may further identify one or more second paced cardiac depolarization waveforms of the one or more second paced cardiac depolarizations. Tachyarrhythmia detection module 71 may then update the one more normal cardiac depolarization waveform morphological templates, e.g., a paced normal template and an intrinsic normal template, based on the one or more second paced cardiac depolarization waveforms using the techniques described above. This updating process may happen continuously, or for a period of time, such as a few months. In other words, tachyarrhythmia detection module 71 may identify new paced and intrinsic normal templates, or update the same, using any of the techniques described herein.

In some examples, tachyarrhythmia detection module 71 may perform a verification process on the paced normal cardiac depolarization waveform morphological template. In some examples, tachyarrhythmia detection module 71 may receive an indication of an intrinsic cardiac depolarization of the patient, wherein the intrinsic cardiac depolarization has a faster heart rate than the normal cardiac depolarization waveform morphological template, and determine an intrinsic cardiac depolarization waveform for the intrinsic cardiac depolarization. Tachyarrhythmia detection module 71 of subcutaneous ICD 30 may then compare the paced normal cardiac depolarization waveform morphological template to the intrinsic cardiac depolarization waveform. Processor 70 may verify that the paced normal cardiac depolarization waveform morphological template is different than the intrinsic cardiac depolarization waveform.

As described herein, components of subcutaneous ICD 30 may be configured to sense a cardiac electrogram of heart 12 of patient 14, identify a plurality of cardiac depolarizations within the cardiac electrogram, and determine that one or more of the cardiac depolarizations are paced cardiac depolarizations resulting from delivery of a pacing pulse to heart 12 by LPD 16 without detecting the pacing pulse and without communicating with LPD 16. Subcutaneous ICD 30 may be further configured to identify one or more paced cardiac depolarization waveforms of the one or more paced cardiac depolarizations, determine a paced cardiac depolarization waveform morphological template based on the one or more identified paced cardiac depolarization waveforms, and determine a normal cardiac depolarization waveform morphological template (e.g., one or both of an intrinsic normal template and a paced normal template) based on the paced cardiac depolarization waveform morphological template. Subcutaneous ICD 30 may be configured to compare the normal cardiac depolarization waveform morphological template to subsequent cardiac depolarization waveforms and detect a cardiac tachyarrhythmia based on the comparison of the normal cardiac depolarization waveform morphological template to subsequent cardiac depolarization waveforms. Examples of methods for detecting a tachyarrhythmia based on templates are generally described in U.S. Pat. No. 5,354,316 (Keimel), U.S. Pat. No. 5,545,186 (Olson, et al.), U.S. Pat. No. 6,393,316 (Gillberg, et al.), U.S. Pat. No. 7,031,771 (Brown, et al.), U.S. Pat. No. 8,160,684 (Ghanem, et al.), U.S. Pat. No. 8,437,842 (Zhang, et al.), U.S. patent application Ser. No. 13/826,097 (Zhang), U.S. patent application Ser. Nos. 14/250,040, 14/487,248, and 14/255,158, each of which is incorporated herein by reference in their entirety.

Figure 5:
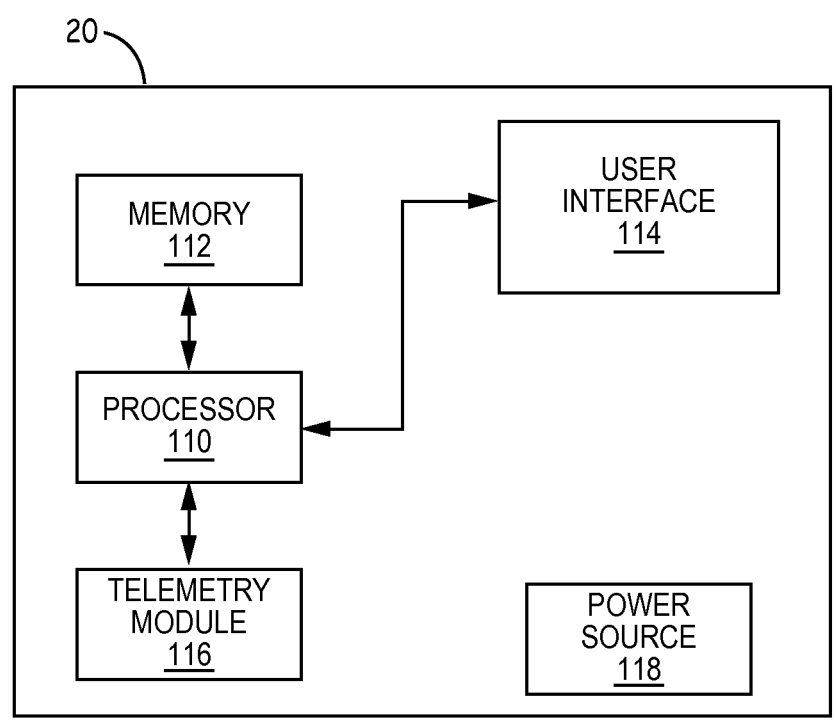
FIG. 5 is a functional block diagram illustrating an example configuration of the programmer of FIG. 1.

FIG. 5 is a functional block diagram illustrating an example configuration of programmer 20 of FIG. 1. As shown in FIG. 5, programmer 20 may include a processor 110, memory 112, user interface 114, telemetry module 116, and power source 118. Programmer 20 may be a dedicated hardware device with dedicated software for programming of LPD 16 and/or subcutaneous ICD 30. Alternatively, programmer 20 may be an off-the-shelf computing device running an application that enables programmer 20 to program LPD 16 and/or subcutaneous ICD 30.

A user may use programmer 20 to configure the operational parameters of and retrieve data from LPD 16 and/or subcutaneous ICD 30 (FIG. 1). In one example, programmer 20 may communicate directly to both LPD 16 and subcutaneous ICD 30. In other examples, programmer may communicate to one of LPD 16 or subcutaneous ICD 30, and that device may relay any instructions or information to or from the other device. The clinician may interact with programmer 20 via user interface 114, which may include display to present graphical user interface to a user, and a keypad or another mechanism for receiving input from a user. In addition, the user may receive an alert or notification from subcutaneous ICD 30 indicating that a shock has been delivered, any other therapy has been delivered, or any problems or issues related to the treatment of patient 14.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 20 herein, and information used by processor 110 to provide the functionality ascribed to programmer 20 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 20 is used to program therapy for another patient.

Programmer 20 may communicate wirelessly with LPD 16 and/or subcutaneous ICD 30, such as using RF communication or proximal inductive interaction. This wireless communication is possible through the use of telemetry module 116, which may be coupled to an internal antenna or an external antenna. An external antenna that is coupled to programmer 20 may correspond to the programming head that may be placed over heart 12 or the location of the intend implant, as described above with reference to FIG. 1. Telemetry module 116 may be similar to telemetry module 74 of FIG. 4. In some examples, telemetry module 116 of programmer 20 may be used for user input, which may be communicated to subcutaneous ICD 30. subcutaneous ICD 30 may receive an indication of user input from programmer 20 that indicates one or more cardiac depolarizations of the plurality of cardiac depolarizations that are paced cardiac depolarizations and determine that the one or more cardiac depolarizations indicated by the indication of user input are paced cardiac depolarizations resulting from delivery of the pacing pulse to the heart by LPD 16 without detecting the pacing pulse and without communicating with LPD 16.

Telemetry module 116 may also be configured to communicate with another computing device via wireless communication techniques, or direct communication through a wired connection. Examples of local wireless communication techniques that may be employed to facilitate communication between programmer 20 and another computing device include RF communication according to the 802.11 or Bluetooth specification sets, infrared communication, e.g., according to the IrDA standard, or other standard or proprietary telemetry protocols. An additional computing device in communication with programmer 20 may be a networked device such as a server capable of processing information retrieved from LPD 16.

Further, programmer 20 could be used to program parameters or instructions for subcutaneous ICD 30 to generate the templates described herein. Also, in some examples, some of the functionality described as being implemented in subcutaneous ICD 30 could be implemented in programmer 20 or another computing device. For example, programmer 20 or another computing device may receive a cardiac electrogram and perform techniques of the current disclosure. In another example, programmer 20 or another computing device could receive the paced and intrinsic waveforms identified by subcutaneous ICD 30, and generate the templates.

Figure 6:
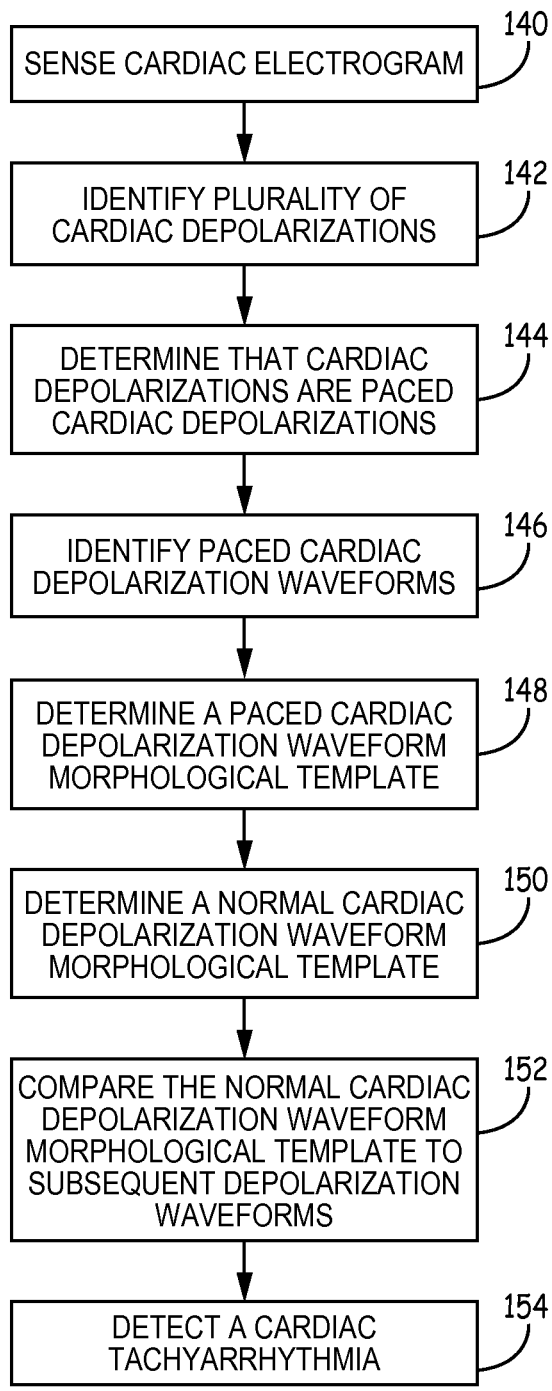
FIG. 6 is a flow diagram of an example technique for determining a paced cardiac depolarization waveform morphological template, in accordance with one or more techniques of the current disclosure.

FIG. 6 is a flow diagram of an example technique for determining a paced cardiac depolarization waveform morphological template, in accordance with one or more techniques of the current disclosure. In the example of FIG. 6, an implantable medical device (e.g., subcutaneous ICD 30) may be configured to sense a cardiac electrogram of a heart (e.g., heart 12) of a patient (e.g., patient 14) (140). Subcutaneous ICD 30 may also be configured to identify a plurality of cardiac depolarizations within the cardiac electrogram (142).

Subcutaneous ICD 30 may be configured to determine that one or more of the cardiac depolarizations are paced cardiac depolarizations resulting from delivery of a pacing pulse to the heart by another implantable medical device (e.g., LPD 16) without detecting the pacing pulse and without communicating with the LPD (144). Subcutaneous ICD 30 may determine that one or more of the cardiac depolarizations are paced cardiac depolarizations through various techniques, which are described below with respect to FIGS. 7A-7F. Subcutaneous ICD 30 may be further configured to identify one or more paced cardiac depolarization waveforms of the one or more paced cardiac depolarizations (146). Subcutaneous ICD 30 may be configured to determine a paced cardiac depolarization waveform morphological template based on the one or more identified paced cardiac depolarization waveforms (148).

Subcutaneous ICD 30 may be further configured to determine one or more normal cardiac depolarization waveform morphological templates based on the paced cardiac depolarization waveform morphological template (150). In the examples provided herein, the one or more normal cardiac depolarization waveform morphological templates may include a paced normal template that models paced cardiac depolarizations and/or an intrinsic normal template that models intrinsic cardiac depolarizations, as both types of cardiac depolarizations may be considered safe and not tachyarrhythmias. In either case, the normal cardiac depolarization waveform morphological template(s) may be based on a paced cardiac depolarization waveform morphological template. For example, in the case of a paced normal cardiac depolarization waveform morphological template that models paced cardiac depolarizations, the paced normal cardiac depolarization waveform morphological template may simply be the paced cardiac depolarization waveform morphological template.

An intrinsic normal cardiac depolarization waveform morphological template that models intrinsic cardiac depolarization waveforms may be determined by comparing cardiac depolarizations to the paced cardiac depolarization waveform morphological template. If the cardiac depolarization matches the paced cardiac depolarization waveform morphological template, then the cardiac depolarization may be discarded. If the cardiac depolarization does not match the paced cardiac depolarization waveform morphological template, then the cardiac depolarization may be a candidate for determining the intrinsic normal cardiac depolarization waveform morphological template. Subcutaneous ICD 30 may determine an intrinsic cardiac depolarization waveform morphological template based on the waveforms of the identified candidate intrinsic cardiac depolarizations.

Subcutaneous ICD 30 may be configured to compare the one or more normal cardiac depolarization waveform morphological templates to subsequent cardiac depolarization waveforms (152). Further, subcutaneous ICD 30 may be configured to detect a cardiac tachyarrhythmia based on the comparison of the normal cardiac depolarization waveform morphological template(s) to subsequent cardiac depolarization waveforms (154).

FIGS. 7A-7F are flow diagrams of example techniques for determining whether a cardiac depolarization is a paced cardiac depolarization, in accordance with one or more techniques of the current disclosure. An IMD (e.g., subcutaneous ICD 30) may be configured to determine that one or more of the cardiac depolarizations are paced cardiac depolarizations resulting from delivery of a pacing pulse to a heart by a LPD (e.g., LPD 16) without detecting the pacing pulse and without communicating with the LPD. The IMD may determine that one or more of the cardiac depolarizations are paced cardiac depolarizations through various tactics. In some examples, the IMD may receive an indication of user input that indicates one or more cardiac depolarizations of the plurality of cardiac depolarizations that are paced cardiac depolarizations. In another example, the IMD may compare each of the plurality of cardiac depolarizations to a stored default paced cardiac depolarization model.

Figure 7A:
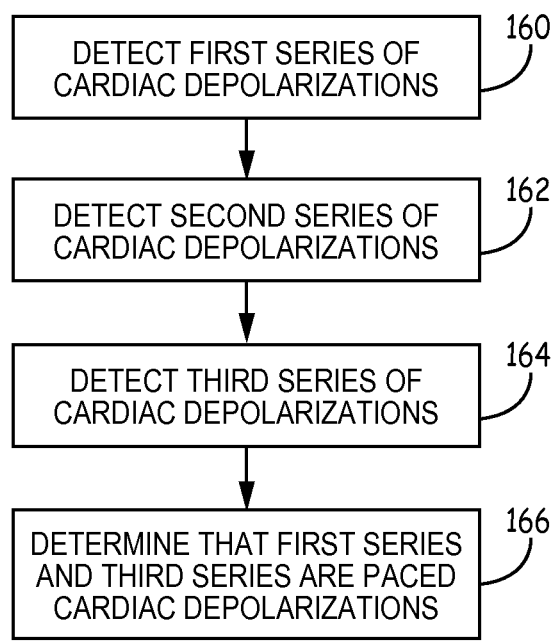
FIGS. 7A-7F are flow diagrams of example techniques for determining whether a cardiac depolarization is a paced cardiac depolarization, in accordance with one or more techniques of the current disclosure.

In the example of FIG. 7A, the IMD may detect a first series of cardiac depolarizations of the plurality of cardiac depolarizations with a first set of beat characteristics (160). In this example, the IMD may further detect a second series of cardiac depolarizations of the plurality of cardiac depolarizations subsequent to the first series of cardiac depolarizations with a second set of beat characteristics different than the first set of beat characteristics (162). The IMD may also detect a third series of cardiac depolarizations of the plurality of cardiac depolarizations subsequent to the second series of cardiac depolarizations with a third set of beat characteristics that are the same as the first set of beat characteristics (164). The IMD may determine that the first series of cardiac depolarizations and the third series of cardiac depolarizations are paced cardiac depolarizations resulting from delivery of the pacing pulse to the heart by the LPD without detecting the pacing pulse and without communicating with the LPD (166). In some examples of this technique, the first set of beat characteristics may comprise a sudden change in ventricular heart rate by a consistent amount over a short run set of beats with morphology stabilizing to a consistent form for the final two beats. In some examples, the short run set of beats may be four beats. The second series of beats are identified by a pause and re-emergence of the pre-elevation heart rate with consistent morphology after the second pre-elevation rate beat. The third series of depolarizations are identified by a similar or greater increase in heart rate to the first series, again with establishment of a stable morphology after a small number of depolarizations at the elevated rate. The IMD may identify the one or more paced cardiac depolarization waveforms of the final two cardiac depolarizations in the first series of cardiac depolarizations or the final two cardiac depolarizations in the third series of cardiac depolarizations as paced depolarizations for determination of a paced cardiac depolarization waveform template. In other examples, the IMD may identify the one or more paced cardiac depolarization waveforms of the final cardiac depolarization in the first series of cardiac depolarizations or the final cardiac depolarization in the third series of cardiac depolarizations as paced depolarizations for determination of a paced cardiac depolarization waveform template. In general, the IMD may identify the one or more paced cardiac depolarization waveforms of the final N cardiac depolarization in the first series of cardiac depolarizations or the final N cardiac depolarization in the third series of cardiac depolarizations, where N is some number of cardiac depolarizations as paced depolarizations for determination of a paced cardiac depolarization waveform template.

Figure 7B:
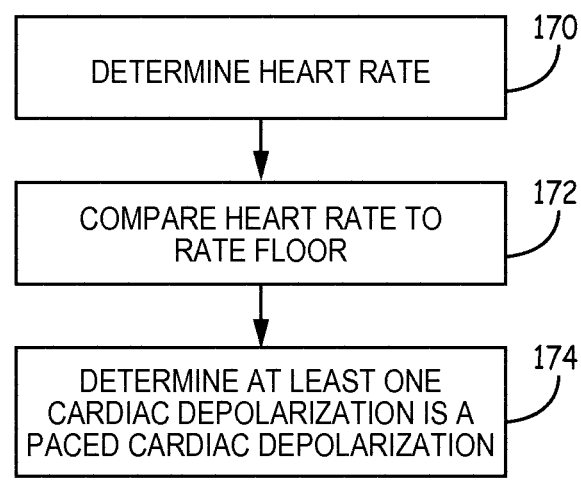

In the example of FIG. 7B, the IMD first determines a heart rate for each of the plurality of cardiac depolarizations and uses various characteristics of the heart rate to determine that the cardiac depolarizations are paces cardiac depolarizations (170). In one example, the IMD may compare the heart rate for each of the plurality of cardiac depolarizations to a rate floor (172). The rate floor, in some examples, may be the slowest possible heart rate at which a pacemaker, e.g., LPD 16 is programmed to pace the heart, e.g., 60 beats-per-minute. In another instance, the rate floor may be any heart rate above the slowest heart rate. In these examples, the IMD may, for at least one cardiac depolarization that has a heart rate within a pre-determined range of the rate floor, determine that the cardiac depolarization is a paced cardiac depolarization resulting from delivery of the pacing pulse to the heart by the LPD without detecting the pacing pulse and without communicating with the LPD (174). For example, the IMD may determine the lowest heart rates over a certain period of time and determine if the heart rate is sustained during that time, such as over 6-8 cardiac cycles. In some examples, the rate floor may be a modulated rate floor. The IMD may further determine an activity level of the patient. For example, the IMD may receive information from an activity sensor and determine a rate floor based on the level of activity detected in the activity sensor. For instance, if the activity sensor is detecting a high amount of activity, the modulated rate floor may be relatively higher. Alternatively, if the activity sensor is detecting a low amount of activity, the modulated rate floor may be relatively lower. In another example, instead of or in addition to activity level, the modulated rate floor may be modulated based on previous measured heart rates.

Figure 7C:
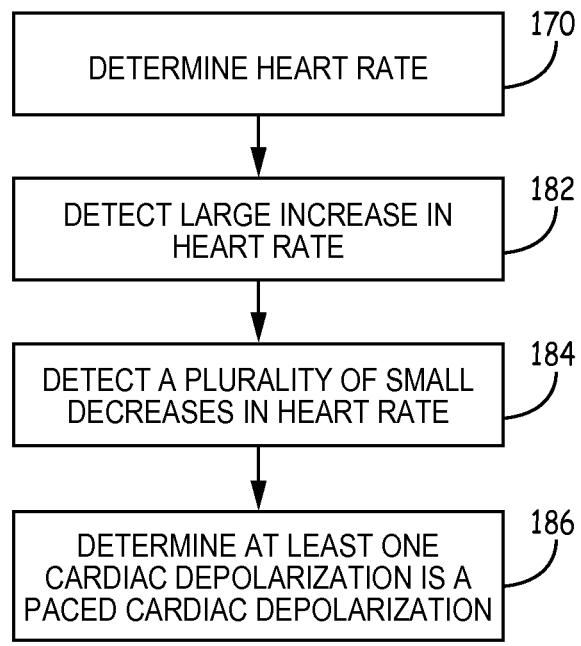

In the example of FIG. 7C, the IMD may detect a large increase in the heart rate between a first pair of consecutive cardiac depolarizations (182). In this example, the IMD may further detect a plurality of small decreases in the heart rate between a plurality of pairs of consecutive cardiac depolarizations subsequent to the first pair of consecutive cardiac depolarizations (184). For example, the heart rate may start as an irregular rapid heartbeat around 95 beats per minute (bpm). The IMD may detect a large increase in the heart rate, such as an increase as large as 50 bpm, followed by a series of small, stable decreases thereafter. An example of such a situation may be seen with respect to FIG. 10, as described below. This may be an indication that the decrease is due to activity from the LPD. Alternatively, if the decreases are irregular or unstable, it may be an arrhythmia. The IMD may then, for at least one cardiac depolarization in the plurality of cardiac depolarizations subsequent to the pair of cardiac depolarizations, determine that the cardiac depolarization is a paced cardiac depolarization resulting from delivery of the pacing pulse to the heart by the LPD without detecting the pacing pulse and without communicating with the LPD (186).

Figure 7D:
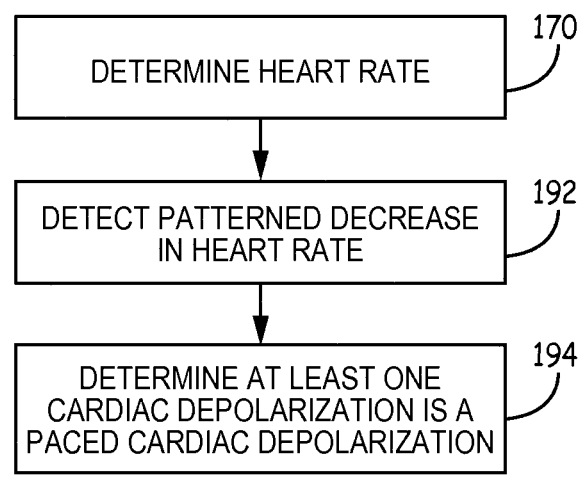

In the example of FIG. 7D, the IMD may detect a patterned decrease in the heart rate amongst a subset of the plurality of cardiac depolarizations, such as a smooth rate decrease of the heart rates or a plurality of decreases by a discrete number of the heart rates (192). If the patterned decrease is sustained for a duration of time across the plurality of cardiac depolarizations, such as for 10-30 seconds, then it may be an indication that the LPD is sending pacing pulses to the heart. This could occur in a case where strenuous activity raises the heart rate of the patient and the LPD is attempting to gradually decrease the heart rate back to a normal rate. In this example, the IMD may, for at least one cardiac depolarization in the subset of cardiac depolarizations, determine that the cardiac depolarization is a paced cardiac depolarization resulting from delivery of the pacing pulse to the heart by the LPD without detecting the pacing pulse and without communicating with the LPD (194). Examples of a patterned decrease can be seen with respect to FIG. 9, as described below.

Figure 7E:
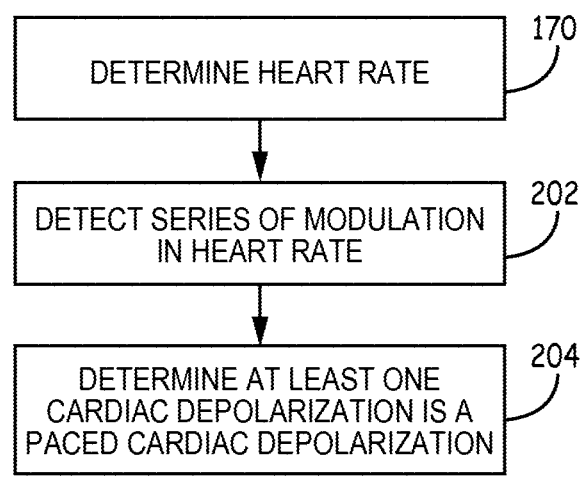

In the example of FIG. 7E, the IMD may detect a series of modulations in the heart rate amongst a subset of the plurality of cardiac depolarizations, wherein the series of modulations comprises an increase by a specific number of beats per minute followed by a decrease by the same specific number of beats per minute (202). This may occur in an instance where the patient has a respiratory sinus arrhythmia, where the LPD may send pacing pules such that the heart rate of the patient may cycle back and forth with a modulation of about 5 bpm. In this example, the IMD may, for at least one cardiac depolarization in the subset of cardiac depolarizations, determine that the cardiac depolarization is a paced cardiac depolarization resulting from delivery of the pacing pulse to the heart by the LPD without detecting the pacing pulse and without communicating with the LPD (204).

Figure 7F:
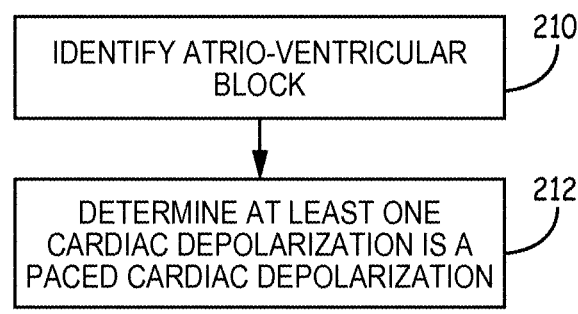

In the example of FIG. 7F, the cardiac depolarizations may comprise ventricular depolarizations, and atrial depolarizations may further be detected. Distinctions between atrial and ventricular depolarizations can be determined by length and amplitude of the respective depolarizations. For example, atrial depolarizations tend to have a lower amplitude over a longer period, while ventricular depolarizations tend to have a larger amplitude over a shorter period. The IMD may identify an atrio-ventricular block based on the atrial depolarizations and the ventricular depolarizations (210). In this example, in response to identifying the atrio-ventricular block, the IMD may determine that at least one of the ventricular depolarizations during the atrio-ventricular block is a paced cardiac depolarization resulting from delivery of the pacing pulse to the heart by the other implantable medical device without detecting the pacing pulse and without communicating with the other implantable medical device (212).

Figure 8:
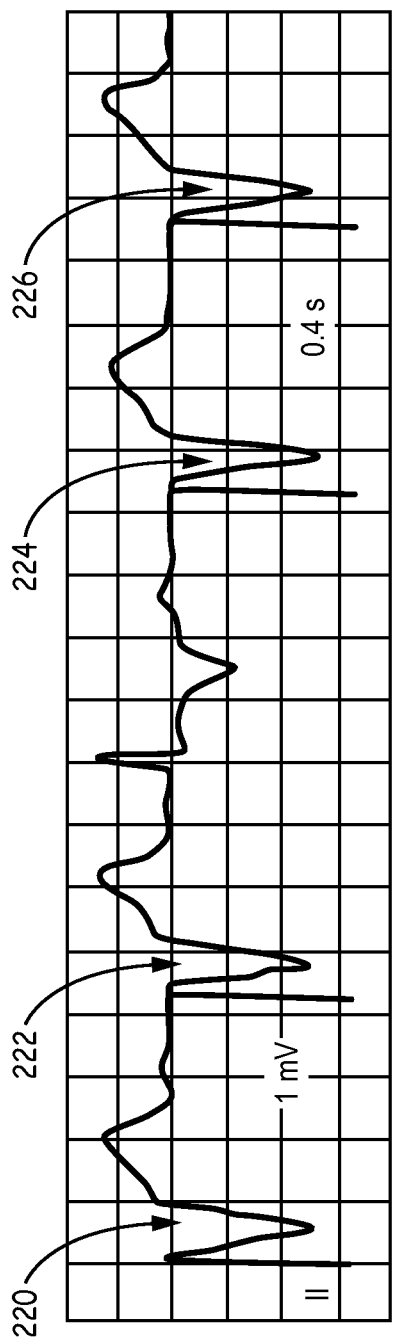
FIG. 8 is a graph illustrating an example paced cardiac depolarization, in accordance with one or more techniques of the current disclosure.

FIG. 8 is a graph illustrating example paced cardiac depolarizations. In this graph, each box represents a vertical scale of 1 mV and a horizontal scale of 0.4 s. As shown in FIG. 8, paced cardiac depolarizations can be seen in the spikes at points 220, 222, 224, and 226.

Figure 9:
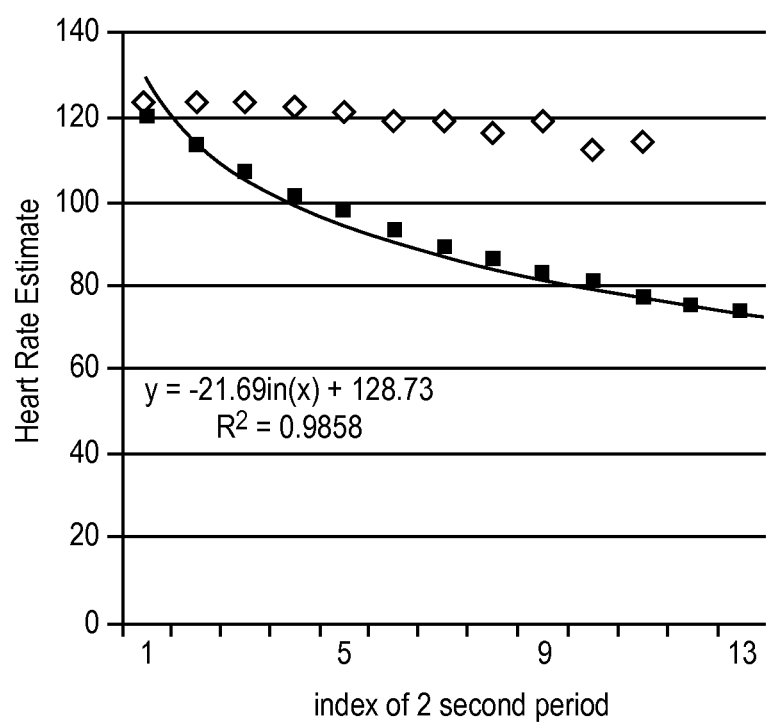
FIG. 9 is a graph illustrating an example paced heart rate deceleration and an example intrinsic heart rate deceleration.

FIG. 9 is a graph illustrating an example deceleration of a heart rate as controlled by a LPD vs. an example intrinsic deceleration of a heart rate. The diamond shapes in the graph of FIG. 9 represent an example intrinsic deceleration of a human heart without the assistance of a pacemaker, such as LPD 16. The decreases are inconsistent and jagged, as the intrinsic heart rate sometimes increases during the process of decreasing. The square shapes and the superimposed regression line show an example deceleration of a human heart as controlled by an artificial pacemaker. The decrease is more consistent, as each step is a consistent decrease from the previous heart rate controlled by an algorithm, and is generally a smooth decrease, as shown by the $R^2$ value of 0.9858 of the regression line. If an IMD, such as subcutaneous ICD 30, detects a cardiac depolarization set that mirrors the squared shapes shown in FIG. 9, the subcutaneous ICD may determine that it is a set of paced cardiac depolarizations, in accordance with techniques described herein.

Figure 10:
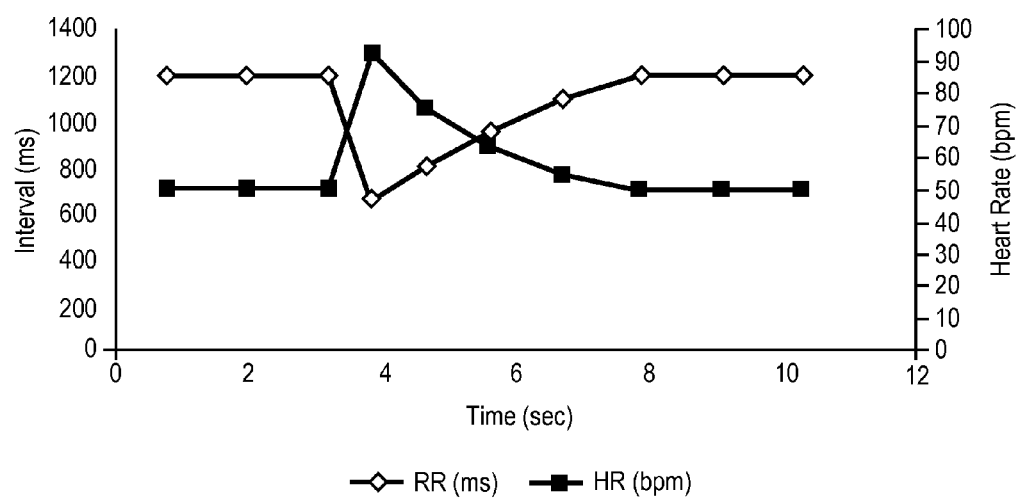
FIG. 10 is a graph illustrating an example of heart rates and R-R intervals resulting from a rate smoothing algorithm responding to a premature atrial or ventricular complex.

FIG. 10 is a graph illustrating an example of heart rates and R-R intervals resulting from a rate smoothing algorithm responding to a premature atrial or ventricular complex, in accordance with one or more techniques of the current disclosure. This heart rate sequence may be used in an example corresponding to the flow diagram of FIG. 7C. As seen by the square shaped points, the heart rate sees a sharp increase of over 40 bpm, followed by a smooth, gradual decrease in heart rate. R-R intervals, represented by the diamond shaped points in FIG. 10, change conversely with the heart rate. This could be an example of a LPD-induced tachycardia, which is a situation in which the subcutaneous ICD should not administer shock therapy. As such, if the subcutaneous ICD detects a cardiac depolarization set that mirrors the graph shown in FIG. 10, the subcutaneous ICD may determine that it is a set of paced cardiac depolarizations, in accordance with techniques described herein.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to subcutaneous ICD 30, LPD 16, programmer 20, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between subcutaneous ICD 30, LPD 16 and/or programmer 20. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples of the disclosure have been described. Any combination of the described operations or functions is contemplated. These and other examples are within the scope of the following claims.

The invention claimed is:

1. A method comprising:
sensing, by an implantable medical device, a cardiac electrogram of a heart of a patient;
identifying, by the implantable medical device, a plurality of cardiac depolarizations within the cardiac electrogram;
determining, by the implantable medical device, that one or more of the cardiac depolarizations are paced cardiac depolarizations resulting from delivery of a pacing pulse to the heart by another implantable medical device without detecting the pacing pulse and without communicating with the other implantable medical device;
identifying, by the implantable medical device, one or more paced cardiac depolarization waveforms of the one or more paced cardiac depolarizations;
determining, by the implantable medical device, a paced normal cardiac depolarization waveform morphological template based on the one or more identified paced cardiac depolarization waveforms;
comparing, by the implantable medical device, the paced normal cardiac depolarization waveform morphological template to subsequent cardiac depolarization waveforms; and
detecting a cardiac tachyarrhythmia based at least on the comparison of the paced normal cardiac depolarization waveform morphological template to subsequent cardiac depolarization waveforms.

2. The method of claim 1, further comprising:
receiving, by the implantable medical device, an indication of an intrinsic cardiac depolarization of the patient, wherein the intrinsic cardiac depolarization has a faster heart rate than the paced normal cardiac depolarization waveform morphological template;
determining, by the implantable medical device, an intrinsic cardiac depolarization waveform for the intrinsic cardiac depolarization;
comparing, by the implantable medical device, the paced normal cardiac depolarization waveform morphological template to the intrinsic cardiac depolarization waveform; and
verifying, by the implantable medical device, that the paced normal cardiac depolarization waveform morphological template is different than the intrinsic cardiac depolarization waveform.

3. The method of claim 1, further comprising:
determining, by the implantable medical device, an intrinsic normal cardiac depolarization waveform morphological template based on the paced normal cardiac depolarization waveform morphological template, wherein determining the intrinsic normal cardiac depolarization waveform morphological template based on the paced normal cardiac depolarization waveform morphological template comprises:
identifying, by the implantable medical device, an intrinsic cardiac depolarization waveform based on a comparison of one or more cardiac depolarizations to the paced normal cardiac depolarization waveform morphological template; and
determining, by the implantable medical device, the intrinsic normal cardiac depolarization waveform morphological template based on the intrinsic cardiac depolarization waveform.

4. The method of claim 1, wherein determining that one or more of the cardiac depolarizations are paced cardiac depolarizations comprises:
determining, by the implantable medical device, a heart rate for each of the plurality of cardiac depolarizations;
comparing, by the implantable medical device, the heart rate for each of the plurality of cardiac depolarizations to a rate floor; and
for at least one cardiac depolarization that has a heart rate within a pre-determined range of the rate floor, determining, by the implantable medical device, that the cardiac depolarization is a paced cardiac depolarization.

5. The method of claim 4, wherein the rate floor is a modulated rate floor, and wherein the method further comprises:
determining, by the implantable medical device, an activity level of the patient; and
determining, by the implantable medical device and based at least in part on the activity level, the modulated rate floor.

6. The method of claim 1, wherein determining that one or more of the cardiac depolarizations are paced cardiac depolarizations comprises:
determining, by the implantable medical device, a heart rate for each of the plurality of cardiac depolarizations;
detecting, by the implantable medical device, a large increase in the heart rate between a first pair of consecutive cardiac depolarizations;
detecting, by the implantable medical device, a plurality of small decreases in the heart rate between a plurality of pairs of consecutive cardiac depolarizations subsequent to the first pair of cardiac depolarizations; and
in response to detecting the plurality of small decreases in the heart rate, determining, by the implantable medical device, that at least one of the cardiac depolarizations in the plurality of pairs of consecutive cardiac depolarizations subsequent to the first pair of cardiac depolarizations is a paced cardiac depolarization.

7. The method of claim 1, wherein determining that one or more of the cardiac depolarizations are paced cardiac depolarizations comprises:
determining, by the implantable medical device, a heart rate for each of the plurality of cardiac depolarizations;
detecting, by the implantable medical device, a patterned decrease in the heart rate amongst a subset of the plurality of cardiac depolarizations; and
in response to detecting the patterned decrease in the heart rate, determining by the implantable medical device, that at least one of the subset of cardiac depolarizations is a paced cardiac depolarization.

8. The method of claim 7, wherein detecting the patterned decrease comprises detecting at least one of a smooth rate decrease of the heart rates or a plurality of decreases by a discrete number of the heart rates.

9. The method of claim 1, wherein the cardiac depolarizations comprise ventricular depolarizations, the method further comprising detecting atrial depolarizations, wherein determining that one or more of the cardiac depolarizations are paced cardiac depolarizations comprises:
identifying an atrio-ventricular block based on the atrial depolarizations and the ventricular depolarizations; and
in response to identifying the atrio-ventricular block, determining, by the implantable medical device, that at least one of the ventricular depolarizations during the atrio-ventricular block is a paced cardiac depolarization.

10. The method of claim 1, wherein determining that one or more of the cardiac depolarizations are paced cardiac depolarizations comprises:
determining, by the implantable medical device, a heart rate for each of the plurality of cardiac depolarizations;
detecting, by the implantable medical device, a series of modulations in the heart rate amongst a subset of the plurality of cardiac depolarizations, wherein the series of modulations comprises an increase by a specific number of beats per minute followed by a decrease by the same specific number of beats per minute; and
in response to detecting the series of modulations, for at least one cardiac depolarization in the subset of cardiac depolarizations, determining, by the implantable medical device, that the cardiac depolarization is a paced cardiac depolarization.

11. The method of claim 1, wherein determining that one or more of the cardiac depolarizations are paced cardiac depolarizations comprises:
detecting, by the implantable medical device, a first series of cardiac depolarizations of the plurality of cardiac depolarizations with a first set of beat characteristics;
detecting, by the implantable medical device, a second series of cardiac depolarizations of the plurality of cardiac depolarizations subsequent to the first series of cardiac depolarizations with a second set of beat characteristics different than the first set of beat characteristics;
detecting, by the implantable medical device, a third series of cardiac depolarizations of the plurality of cardiac depolarizations subsequent to the second series of cardiac depolarizations with a third set of beat characteristics that are the same as the first set of beat characteristics; and determining, by the implantable medical device, that the first series of cardiac depolarizations and the third series of cardiac depolarizations are paced cardiac depolarizations.

12. The method of claim 11, wherein the first set of beat characteristics comprises a sudden change in a ventricular heart rate by a consistent amount over a first portion of the first series of cardiac depolarizations followed by a stabilization to a consistent form over a second portion of the first series of cardiac depolarizations.

13. The method of claim 1, wherein the implantable medical device is a subcutaneous implantable cardioverter defibrillator (subcutaneous ICD) and the other implantable medical device is a leadless pacing device (LPD).

14. The method of claim 1, further comprising:
determining, by the implantable medical device, an intrinsic normal cardiac depolarization waveform morphological template based on one or more identified intrinsic cardiac depolarization waveforms within the cardiac electrogram; and
comparing, by the implantable medical device, the intrinsic normal cardiac depolarization waveform morphological template to subsequent cardiac depolarization waveforms,
wherein detecting the cardiac tachyarrhythmia comprises detecting the cardiac tachyarrhythmia based on the comparison of the paced normal cardiac depolarization waveform morphological template and the intrinsic normal cardiac depolarization template to subsequent cardiac depolarization waveforms.

15. An implantable medical device (IMD), the IMD comprising:
a housing configured to be implanted in a patent external to a rib cage of the patient;
one or more electrodes configured to be disposed external to the rib cage;
a sensing module configured to sense a cardiac electrogram of a heart of the patient; and
a tachyarrhythmia detection module configured to:
identify a plurality of cardiac depolarizations within the cardiac electrogram;
determine that one or more of the cardiac depolarizations are paced cardiac depolarizations resulting from delivery of a pacing pulse to the heart by another implantable medical device without detecting the pacing pulse and without communicating with the other implantable medical device;
identify one or more paced cardiac depolarization waveforms of the one or more paced cardiac depolarizations;
determine a paced normal cardiac depolarization waveform morphological template based on the one or more identified paced cardiac depolarization waveforms;
compare the paced normal cardiac depolarization waveform morphological template to subsequent cardiac depolarization waveforms; and
detect a cardiac tachyarrhythmia based at least on the comparison of the paced normal cardiac depolarization waveform morphological template to subsequent cardiac depolarization waveforms.

16. The IMD of claim 15, wherein the tachyarrhythmia detection module is further configured to:

receive an indication of an intrinsic cardiac depolarization of the patient, wherein the intrinsic cardiac depolarization has a faster heart rate than the paced normal cardiac depolarization waveform morphological template;
determine an intrinsic cardiac depolarization waveform for the intrinsic cardiac depolarization;
compare the paced normal cardiac depolarization waveform morphological template to the intrinsic cardiac depolarization waveform; and
verify that the paced normal cardiac depolarization waveform morphological template is different than the intrinsic cardiac depolarization waveform.

17. The IMD of claim 15, wherein the tachyarrhythmia detection module is further configured to determine an intrinsic normal cardiac depolarization waveform morphological template based on the paced normal cardiac depolarization waveform morphological template, wherein the tachyarrhythmia detection module being configured to determine the intrinsic normal cardiac depolarization waveform morphological template based on the paced normal cardiac depolarization waveform morphological template comprises the tachyarrhythmia detection module being configured to:
identify an intrinsic cardiac depolarization waveform based on a comparison of one or more cardiac depolarizations to the paced normal cardiac depolarization waveform morphological template; and
determine the intrinsic normal cardiac depolarization waveform morphological template based on the intrinsic cardiac depolarization waveform.

18. The IMD of claim 15, wherein the tachyarrhythmia detection module being configured to determine that one or more of the cardiac depolarizations are paced cardiac depolarizations comprises the tachyarrhythmia detection module being configured to:
determining, by the implantable medical device, a heart rate for each of the plurality of cardiac depolarizations;
comparing, by the implantable medical device, the heart rate for each of the plurality of cardiac depolarizations to a rate floor; and
for at least one cardiac depolarization that has a heart rate within a pre-determined range of the rate floor, determine that the cardiac depolarization is a paced cardiac depolarization.

19. The IMD of claim 18, wherein the rate floor is a modulated rate floor, and wherein the tachyarrhythmia detection module is further configured to:
determine an activity level of the patient; and
determine, based at least in part on the activity level, the modulated rate floor.

20. The IMD of claim 15, wherein the tachyarrhythmia detection module being configured to determine that one or more of the cardiac depolarizations are paced cardiac depolarizations comprises the tachyarrhythmia detection module being configured to:
determine a heart rate for each of the plurality of cardiac depolarizations;
detect a large increase in the heart rate between a first pair of consecutive cardiac depolarizations;
detect a plurality of small decreases in the heart rate between a plurality of pairs of consecutive cardiac depolarizations subsequent to the first pair of cardiac depolarizations; and
in response to detecting the plurality of small decreases in the heart rate, determine that at least one of the cardiac depolarizations in the plurality of pairs of consecutive cardiac depolarizations subsequent to the first pair of cardiac depolarizations is a paced cardiac depolarization.

21. The IMD of claim 15, wherein the tachyarrhythmia detection module being configured to determine that one or more of the cardiac depolarizations are paced cardiac depolarizations comprises the tachyarrhythmia detection module being configured to:
   determine a heart rate for each of the plurality of cardiac depolarizations;
   detect a patterned decrease in the heart rate amongst a subset of the plurality of cardiac depolarizations; and
   in response to detecting the patterned decrease in the heart rate, determine that at least one of the subset of cardiac depolarizations is a paced cardiac depolarization.

22. The IMD of claim 21, wherein the tachyarrhythmia detection module being configured to detect the patterned decrease comprises the tachyarrhythmia detection module being configured to detect at least one of a smooth rate decrease of the heart rates or a plurality of decreases by a discrete number of the heart rates.

23. The IMD of claim 15, wherein the cardiac depolarizations comprise ventricular depolarizations, wherein the tachyarrhythmia detection module is further configured to detect atrial depolarizations, and wherein the tachyarrhythmia detection module being configured to determine that one or more of the cardiac depolarizations are paced cardiac depolarizations comprises the tachyarrhythmia detection module being configured to:
   identify an atrio-ventricular block based on the atrial depolarizations and the ventricular depolarizations; and
   in response to identifying the atrio-ventricular block, determine that at least one of the ventricular depolarizations during the atrio-ventricular block is a paced cardiac depolarization.

24. The IMD of claim 15, wherein the tachyarrhythmia detection module being configured to determine that one or more of the cardiac depolarizations are paced cardiac depolarizations comprises the tachyarrhythmia detection module being configured to:
   determine a heart rate for each of the plurality of cardiac depolarizations;
   detect a series of modulations in the heart rate amongst a subset of the plurality of cardiac depolarizations, wherein the series of modulations comprises an increase by a specific number of beats per minute followed by a decrease by the same specific number of beats per minute; and
   in response to detecting the series of modulations, for at least one cardiac depolarization in the subset of cardiac depolarizations, determine that the cardiac depolarization is a paced cardiac depolarization.

25. The IMD of claim 15, wherein the tachyarrhythmia detection module being configured to determine that one or more of the cardiac depolarizations are paced cardiac depolarizations comprises the tachyarrhythmia detection module being configured to:
   detect a first series of cardiac depolarizations of the plurality of cardiac depolarizations with a first set of beat characteristics;
   detect a second series of cardiac depolarizations of the plurality of cardiac depolarizations subsequent to the first series of cardiac depolarizations with a second set of beat characteristics different than the first set of beat characteristics;
   detect a third series of cardiac depolarizations of the plurality of cardiac depolarizations subsequent to the second series of cardiac depolarizations with a third set of beat characteristics that are the same as the first set of beat characteristics; and
   determine that the first series of cardiac depolarizations and the third series of cardiac depolarizations are paced cardiac depolarizations.

26. The IMD of claim 25, wherein the first set of beat characteristics comprises a sudden change in a ventricular heart rate by a consistent amount over a first portion of the first series of cardiac depolarizations followed by a stabilization to a consistent form over a second portion of the first series of cardiac depolarizations.

27. The IMD of claim 15, wherein the IMD is a subcutaneous implantable cardioverter defibrillator (subcutaneous ICD).

28. The IMD of claim 15, wherein the tachyarrhythmia detection module is further configured to:
   determine an intrinsic normal cardiac depolarization waveform morphological template based on one or more identified intrinsic cardiac depolarization waveforms within the cardiac electrogram; and
   compare the intrinsic normal cardiac depolarization waveform morphological template to subsequent cardiac depolarization waveforms,
   wherein the tachyarrhythmia detection module being configured to detect the cardiac tachyarrhythmia comprises the tachyarrhythmia detection module being configured to detect the cardiac tachyarrhythmia based on the comparison of the paced normal cardiac depolarization waveform morphological template and the intrinsic normal cardiac depolarization template to subsequent cardiac depolarization waveforms.

29. A device comprising:
   means for sensing a cardiac electrogram of a heart of a patient;
   means for identifying a plurality of cardiac depolarizations within the cardiac electrogram;
   means for determining that one or more of the cardiac depolarizations are paced cardiac depolarizations resulting from delivery of a pacing pulse to the heart by another implantable medical device without detecting the pacing pulse and without communicating with the other implantable medical device;
   means for identifying one or more paced cardiac depolarization waveforms of the one or more paced cardiac depolarizations;
   means for determining a paced normal cardiac depolarization waveform morphological template based on the one or more identified paced cardiac depolarization waveforms;
   means for comparing the paced normal cardiac depolarization waveform morphological template to subsequent cardiac depolarization waveforms; and
   means for detecting a cardiac tachyarrhythmia based at least on the comparison of the paced normal cardiac depolarization waveform morphological template to subsequent cardiac depolarization waveforms.

* * * * *